United States Patent
Folkerts et al.

(10) Patent No.: US 12,322,486 B1
(45) Date of Patent: Jun. 3, 2025

(54) APPROACHES TO IMPROVING THE RELIABILITY OF WIRELESS CONNECTIONS BETWEEN MEDICATION CONTAINERS AND CENTRAL COMPUTING DEVICES

(71) Applicant: Verily Life Sciences LLC, Mountain View, CA (US)

(72) Inventors: Madeline Folkerts, San Francisco, CA (US); Jasper Lodewyk Steyn, San Francisco, CA (US)

(73) Assignee: Verily Life Sciences LLC, Dallas, TX (US)

(*) Notice: Subject to any disclaimer, the term of this patent is extended or adjusted under 35 U.S.C. 154(b) by 602 days.

(21) Appl. No.: 17/669,566

(22) Filed: Feb. 11, 2022

Related U.S. Application Data

(60) Provisional application No. 63/148,556, filed on Feb. 11, 2021.

(51) Int. Cl.
*G16H 20/13* (2018.01)
*A61J 7/00* (2006.01)
*H04W 4/35* (2018.01)
*H04W 4/80* (2018.01)

(52) U.S. Cl.
CPC .......... *G16H 20/13* (2018.01); *A61J 7/0076* (2013.01); *H04W 4/35* (2018.02); *H04W 4/80* (2018.02)

(58) Field of Classification Search
CPC .......... G16H 20/13; H04W 4/35; H04W 4/80; A61J 7/0076

USPC .................................................. 340/539.12
See application file for complete search history.

(56) References Cited

U.S. PATENT DOCUMENTS

| | | | | |
|---|---|---|---|---|
| 6,937,617 | B2* | 8/2005 | Rakib | H04N 7/10 370/479 |
| 6,983,031 | B2* | 1/2006 | Wheatley | H04L 7/042 375/368 |
| 7,366,675 | B1* | 4/2008 | Walker | G06Q 10/109 705/2 |
| 8,046,072 | B2* | 10/2011 | Fuller | A61N 1/37254 340/517 |
| 9,019,098 | B2* | 4/2015 | Okano | G16H 40/67 340/539.12 |
| 10,124,182 | B2* | 11/2018 | Kivi | A61N 1/36 |
| 2009/0294521 | A1* | 12/2009 | de la Huerga | A61J 1/035 235/375 |
| 2012/0056000 | A1 | 3/2012 | Shores | |
| 2013/0218588 | A1* | 8/2013 | Kehr | G16H 40/63 705/2 |

(Continued)

Primary Examiner — Zhen Y Wu
(74) Attorney, Agent, or Firm — Perkins Coie LLP

(57) ABSTRACT

Introduced here are computer programs and associated computer-implemented techniques for establishing and then maintaining robust wireless communication channels established in accordance with short-range communication protocols. At a high level, two approaches to improving the reliability of these wireless communication channels are described herein. The first approach involves implementing a synchronization scheme in which data is transferred from the container as a series of messages that are arranged in order of increasing payload size and/or decreasing payload priority. The second approach involves employing a wrapper function that is programmed to track the status of wireless connectivity on a more granular level than traditional operating systems.

17 Claims, 16 Drawing Sheets

(56) References Cited

U.S. PATENT DOCUMENTS

| | | | | |
|---|---|---|---|---|
| 2014/0169162 A1* | 6/2014 | Romano | ............... | A61B 5/0015 |
| | | | | 370/230 |
| 2014/0263425 A1* | 9/2014 | Akdogan | ........... | B65D 83/0409 |
| | | | | 222/23 |
| 2014/0370879 A1* | 12/2014 | Redding | ........... | H04M 3/42178 |
| | | | | 455/419 |
| 2017/0083686 A1* | 3/2017 | Hawkins | ............... | G06Q 10/087 |
| 2017/0292757 A1* | 10/2017 | Weaver | ................... | A61J 1/165 |
| 2018/0349561 A1* | 12/2018 | Lecamus | ................ | G16H 20/13 |
| 2020/0413334 A1* | 12/2020 | Kharvar | ................ | H04W 76/14 |

* cited by examiner

800

801

Broadcast a signal to indicate willingness to perform synchronization

802

Receive first input indicative of a response to the signal from a computer program executing on a computing device

803

Cause transmission of a first message whose payload is a first size to the computing device via a wireless communication channel

804

Receive second input indicative of an acknowledgement that the first message was received by the computer program

805

Cause transmission of a second message whose payload is a second size to the computing device via the wireless communication channel

Discover a signal that is locally broadcast by a container that has medication stored therein

902

Determine that the signal indicates data is available for download from the container

903

Initiate a wireless communication channel over which the data can be acquired from the container

904

Receive, via the wireless communication channel, a plurality of messages from the container that contain the data in corresponding payloads

FIGURE 9

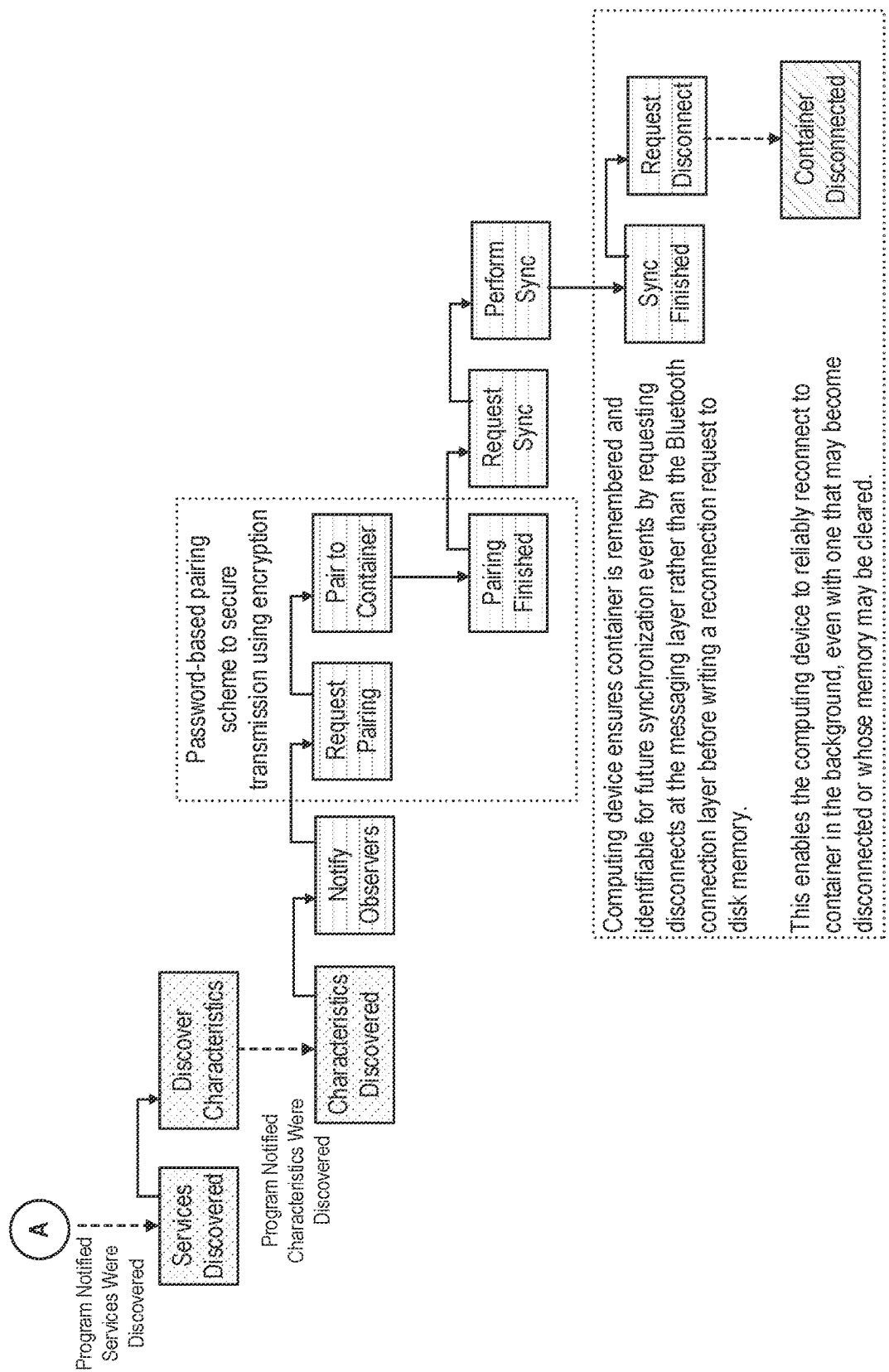
FIGURE 13, CONT.

ations of the medication so that compliance with a
regimen can be determined.
APPROACHES TO IMPROVING THE RELIABILITY OF WIRELESS CONNECTIONS BETWEEN MEDICATION CONTAINERS AND CENTRAL COMPUTING DEVICES

CROSS-REFERENCE TO RELATED APPLICATIONS

This application claims priority to U.S. Provisional Application No. 63/148,556, titled "Approaches to Improving the Reliability of Wireless Connections Between Medication Containers and Central Computing Devices" and filed on Feb. 11, 2021, which is incorporated by reference herein in its entirety.

TECHNICAL FIELD

Various embodiments concern computer programs and associated computer-implemented techniques for establishing and then maintaining robust wireless connections over short-range communication protocols.

BACKGROUND

A pill organizer (also referred to as a "pill container" or "pill box") is a multi-compartment aid that is designed to promote compliance with a regimen by storing scheduled doses of one or more medications. Many pill organizers have at least one compartment for each day of the week, though other versions have been developed. Some pill organizers have multiple compartments corresponding to different times of the day. For example, a pill organizer could include a first row of seven compartments in which medications to be administered in the morning are placed and a second row of seven compartments in which medications to be administered in the evening are placed.

Historically, pill organizers have been viewed as a convenient way to reduce the number of errors associated with administrations of the medication(s) required by a regimen. Such errors include administering an improper dose of the appropriate medicine, administering a dose of the appropriate medicine at the wrong time, and administering the wrong medicine altogether. However, evidence of effectiveness of these pill organizers is not strong.

BRIEF DESCRIPTION OF THE DRAWINGS

FIG. 8 includes a flow diagram of a process for transferring data from a container in which medication is stored to a computing device.

FIG. 9 includes a flow diagram of a process for acquiring data from a container in which medication is stored.

Figure 1B:
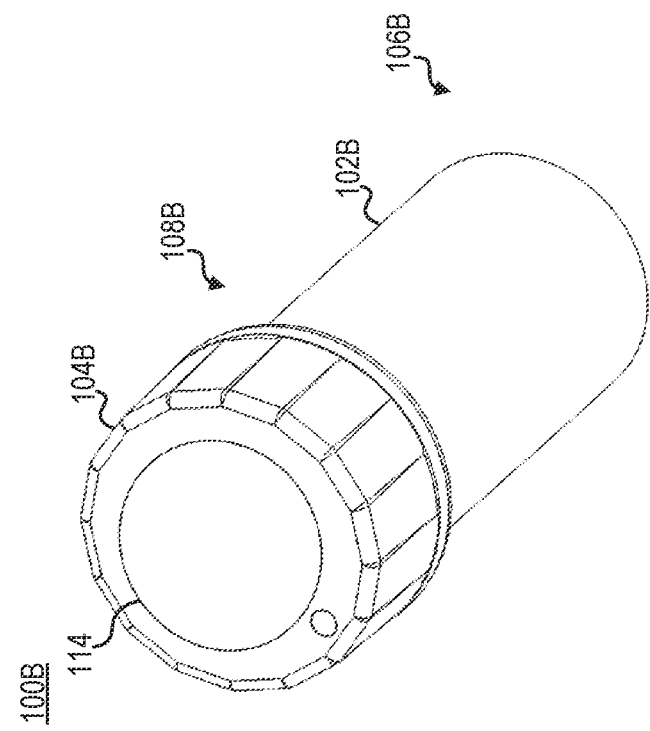
FIGS. 1A-B are perspective views of containers with display units for conveying information regarding usage or the medication stored therein.

Various features of the technologies described herein will become more apparent to those skilled in the art from a study of the Detailed Description in conjunction with the drawings. Embodiments are illustrated by way of example and not limitation in the drawings. While the drawings depict various embodiments for the purpose of illustration, those skilled in the art will recognize that alternative embodiments may be employed without departing from the general principles of the technologies. Accordingly, while specific embodiments are shown in the drawings, the technologies are amenable to various modifications.

DETAILED DESCRIPTION

To address the drawbacks of pill organizers, entities have begun developing electronic pill bottles that alert individuals (also referred to as "patients," "subjects," or "users") when a dose of a medication should be administered. Rather than include separate compartments for doses to be administered over an interval of time (e.g., a week), an electronic pill bottle will generally include a single cavity in which a bulk supply of medication is stored. Normally, electronic pill bottles are able to communicate with central computing devices (or simply "computing devices") over a network. As such, electronic pill bottles may be referred to as "network-connected bottles" or "smart bottles."

An electronic pill bottle may be able to communicate with a computer program that is executing on a computing device. For example, an electronic pill bottle may transmit data regarding administrations of medication to a mobile application that is executing on a mobile phone associated with the individual who is responsible for administering the medication. The computer program may promote compliance with a regimen by generating notifications that alert the individual when doses of medication are due to be administered.

Historically, electronic pill bottles have been designed with several goals in mind. First, an electronic pill bottle should be able to address forgetfulness through on-device notifications that can be readily understood. Generally, the term "on-device" refers to notifications that are presented by the electronic pill bottle itself, though the term could also be used to refer to notifications that are presented by a computing device (e.g., a mobile phone) that is communicatively connected to the electronic pill bottle. Second, an electronic pill bottle should be able to record data related to administrations of medication so that adherence to a regimen can be tracked.

Electronic pill bottles have struggled to accomplish these goals in a consistent, predictable manner, however. Assume, for example, that an individual is prescribed a regimen that requires multiple medications, each contained in a separate electronic pill bottle, be administered over an extended period of time. To monitor adherence to the regimen, the individual may download a computer program to a computing device that is readily accessible. The computing device may be, for example, a tablet computer, mobile phone, or wearable electronic device. As mentioned above, the electronic pill bottles may transmit data regarding administrations of the corresponding medications to the computing device. However, this may not be possible if the computing device is not proximate to the electronic pill bottles. For example, if the individual were to leave her home immediately after administering the medications, wireless communication channels established between the computing device and electronic pill bottles may be disrupted. Monitoring adherence is difficult, if not impossible, if the data generated by the electronic pill bottles fails to reach the computing device in a reliable manner.

Introduced here, therefore, are computer programs and associated computer-implemented techniques for establishing and then maintaining robust wireless connections over short-range communication protocols. For the purpose of illustration, embodiments are described in the context of facilitating the transfer of data from a container in which medication is stored or its closure to a central computing device. While the container may be described as a cylindrical bottle having a cavity defined therein for storing a bulk supply of medication in the form of tablets, those skilled in the art will recognize that the technology is similarly applicable to other forms of medication packages. Aspects of the technology could be implemented in inhalers, insulin pens, insulin pumps, and the like.

Two approaches for improved transfer of data from containers to central computing devices (or simply "computing devices") are described herein.

The first approach involves implementing a synchronization scheme that is robust to intermittent connections. As further discussed below, a container may generate data over time that is related to administrations of the medication stored therein. To determine whether an individual is administering the medication in compliance with a regimen, a computer program that is executing on a computing device may request that the data be downloaded from the container. The data may be transferred from the container to the computer program through a request-response pattern in which the computer program sends a request message to the container and then the container responds with a response message. Oftentimes, multiple response messages are required in order to send all of the data. However, this can be problematic if the connection between the container and computing device is inconsistent as some of the data may be inadvertently lost. Moreover, because the data is normally transferred in a manner that is ambivalent to priority (e.g., from oldest to newest, or vice versa), the importance of the lost data may be difficult, if not impossible, to determine. The scheme described below addresses these concerns by coordinating the transfer of data from the container to the computing device such that a smaller amount of data is transferred during the initial synchronization event. After each successful synchronization event, the payload size can be increased so that larger amounts of data are transferred to the computing device.

The second approach involves employing a wrapper function (or simply "wrapper") to improve the reliability of connections established in accordance with a short-range communication protocol. Assume, for example, that a container has been programmed to transfer data related to administrations of medication to a computing device over a wireless channel established in accordance with the Bluetooth® technology standard (or simply "Bluetooth"). It is important that the container is able to reliably connect to a computer program executing on the computing device in the background so that data received from the container is up to date. While the computer program will generally not be open at the time of synchronization, it is important that the computer program obtain data from the container in near real time to have a full understanding of whether the medication is being administered appropriately. It is often desirable that this communication be secure and not prone to interruptions. It is easy for the wireless channel between the container and computing device to be disrupted, however. To prevent unauthorized disruption, a security layer may be added to the communication protocol. The addition of a security layer, such as, for example, a private advertising scheme, adds complexity when establishing a connection and therefore increases the likelihood of an error occurring during the connection process. As further discussed below, the wrapper addresses this issue by employing a state tracking scheme to resolve intermittent connectivity.

Embodiments may be described with reference to particular computing devices, network configurations, networks, and the like. However, those skilled in the art will recognize that the features may be similarly applicable to other computing devices, network configurations, networks, etc. For example, aspects of the technology may be described in the context of a container that is connected, via Bluetooth, to a mobile phone on which a mobile application is executing. However, the container could be connected to other types of central computing devices, such as tablet computers, wearable electronic devices, etc. Thus, aspects of the technology may be implemented by other types of computer programs, such as desktop applications, over-the-top (OTT) applications, or web browsers.

While embodiments may be described in the context of computer-executable instructions, aspects of the technology can be implemented via hardware, firmware, or software. As an example, operations may be executed by a container to more reliably wirelessly transfer data to a computer program that is executing on a computing device. These operations may be tightly linked with hardware components that are housed in the container, so these operations may be embodied as firmware that is permanently programmed into read-only memory. Thus, the container may include firmware that, upon being executed by a processor, serves to ensure that data is transferred as a series of messages in terms of increasing size or priority. The terms "message," as used herein, refers to a communication that includes a set of data that is sent from a source (e.g., the container) to a destination (e.g., the computing device). The set of data to be included in each message may be identified or determined through a "chunking" process in which the data available to the source is separated into multiple sets.

Terminology

References in this description to "an embodiment" or "one embodiment" means that the particular feature, function, structure, or characteristic being described is included in at least one embodiment. Occurrences of such phrases do not necessarily refer to the same embodiment, nor are they necessarily referring to alternative embodiments that are mutually exclusive of one another.

Unless the context clearly requires otherwise, the words "comprise" and "comprising" are to be construed in an inclusive sense rather than an exclusive or exhaustive sense (i.e., in the sense of "including but not limited to"). The term "based on" is also to be construed in an inclusive sense rather than an exclusive or exhaustive sense. Thus, unless otherwise noted, the term "based on" is intended to mean "based at least in part on."

The terms "connected," "coupled," or any variant thereof is intended to include any connection or coupling between two or more elements, either direct or indirect. The connection/coupling can be physical, logical, or a combination thereof. For example, objects may be electrically or communicatively coupled to one another despite not sharing a physical connection.

The term "module" refers broadly to software components, firmware components, and/or hardware components. Modules are typically functional components that generate output(s) based on specified input(s). A computer program may include one or more modules. Thus, a computer program may include multiple modules responsible for completing different tasks or a single module responsible for completing all tasks.

When used in reference to a list of multiple items, the word "or" is intended to cover all of the following interpretations: any of the items in the list, all of the items in the list, and any combination of items in the list.

The sequences of steps performed in any of the processes described here are exemplary. However, unless contrary to physical possibility, the steps may be performed in various sequences and combinations. For example, steps could be added to, or removed from, the processes described here. Similarly, steps could be replaced or reordered. Thus, descriptions of any processes are intended to be open-ended.

Overview of Network-Connected Container

One example of a network-connected container is described below with respect to FIGS. 1-6 for the purpose of illustration. Those skilled in the art will recognize that the approaches described herein for improved transfer of data could be implemented by other types of network-connected containers. Further information on network-connected containers can be found in U.S. Provisional Application No. 63/088,285, titled "Network-Connected Containers Having Medication Stored Therein," which is incorporated by reference herein in its entirety.

Figure 1A:
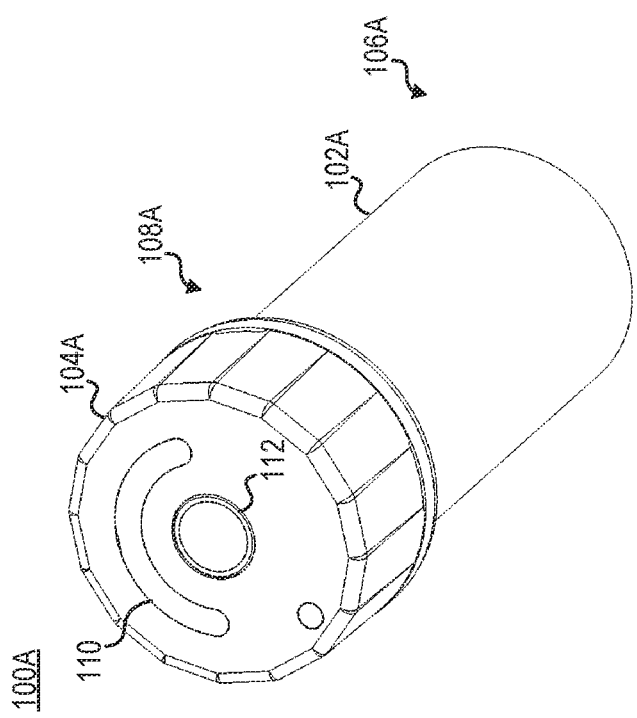

FIGS. 1A-B are perspective views of containers 100A-B with display units for conveying information regarding usage or the medication stored therein. In FIG. 1A, the information display unit is comprised of several illuminants located beneath an arcuate aperture 110 as further discussed below. In FIG. 1B, the information display unit is a display panel 114 comprised of light-emitting diodes (LEDs), organic LEDs, liquid crystal elements, or electrophoretic elements. In some embodiments, the display panel 114 may be touch sensitive. Thus, an individual may be able to provide input to the container 100B shown in FIG. 1B via the display panel 114. The information display units may be used to display the time elapsed since the containers 100A-B were last opened. Additionally or alternatively, the information display unit may be used to notify an individual when the medication that is stored therein is due to be administered.

The containers 100A-B have a durable housing. Generally, the durable housing includes a structural body 102A-B (also referred to as a "base") having a cavity defined therein for storing a bulk supply of medication and a cap 104A-B that is detachably connectable to the structural body 102A-B. When secured to the structural body 102A-B, the cap 104A-B encloses the cavity to retain the bulk supply of medication in the form of pills, powder, etc. Portions of the structural body 102A-B or cap 104A-B may be faceted or ribbed to improve the ease with which the containers 100A-B can be handled. It should be obvious to those skilled in the art that similar containers may be envisioned for medications in liquid, gel, aerosol, or other forms.

The structural body 102A-B may be in the form of a right circular hollow cylinder (also referred to as a "cylindrical shell") defined by a pair of right circular cylinders that share an axis in common and a base perpendicular to the common axis. The base may be located at a first end 106A-B (also referred to as the "distal end") of the cylindrical shell, and an aperture may be located at a second end 108A-B (also referred to as the "proximal end") of the cylindrical shell. In such embodiments, the second end 108A-B may be designed to accommodate the cap 104A-B. Those skilled in the art will recognize that hardware, firmware, and software components could be housed in either the structural body 102A-B or cap 104A-B. Accordingly, unless otherwise noted, the components described herein could be located in the structural body 102A-B or cap 104A-B.

As shown in FIGS. 1A-B, the container 100A-B includes an information display unit able to visually convey information, such as the time elapsed since the container was last opened or the time until the next administration of medication, to a user.

In FIG. 1A, the container 100A includes one or more illuminants that are located beneath an arcuate aperture 110 in the durable housing. The arcuate aperture 110 may be formed along the top of the cap 104A, or the arcuate aperture 110 may be formed along the side of the structural body 102A. These illuminant(s) can be driven to emit light to convey information regarding the medication stored therein. As an example, a series of illuminants may be sequentially driven over time to visually convey information regarding usage of the container 100A. For instance, if the container 100A includes 6 illuminants, another illuminant may be driven every 2 hours to indicate when the container 100A was last opened. Thus, a first illuminant may be driven beginning 2 hours after the container 100A was last opened, a second illuminant may be driven beginning 4 hours after the container 100A was last opened, etc. As another example, a series of illuminants may be sequentially driven over time to visually convey information regarding the regimen. For instance, if the container 100A includes 6 illuminants and medication is to be administered every 12 hours, another illuminant may be driven every 2 hours to visually indicate when the next dose should be administered.

In some embodiments each illuminant located beneath the arcuate aperture 110 is configured to emit light of the same color, while in other embodiments each illuminant located beneath the arcuate aperture 110 is configured to emit light of a different color.

In FIG. 1B, meanwhile, the container 100B includes a display panel 114 comprised of LEDs, organic LEDs, liquid crystal elements, or electrophoretic elements. The display panel 114 may be able to convey similar information as the LED(s) located beneath the arcuate aperture 110 shown in FIG. 1A. However, the display panel 114 may be able to present information in textual form. For example, the display panel 114 may present the actual time elapsed since the container 100B was last opened rather than an approximation of the time elapsed (e.g., where one illuminant is representative of at least two hours, two illuminants is representative of at least four hours, etc.). In some embodiments, the display panel 114 is touch sensitive. Thus, an individual may be able to provide input to the container 100B via the display panel 114.

In FIG. 1A, the cap 104A includes a tactile element 112 through which input can be provided. While not shown, the cap 104B shown in FIG. 1B could also include a tactile element. Accordingly, while the tactile element 112 may be discussed with reference to FIG. 1A, those skilled in the art will recognize that the tactile element 112 could be included in other embodiments of containers (e.g., those with display panels). Alternatively, another feature (e.g., the display panel 114) may be sensitive to touch, and therefore serve a similar purpose. To improve ease of use, some embodiments of the cap include a single centrally located tactile element 112 as shown in FIG. 1A. In other embodiments, the tactile element 112 is one of multiple tactile elements positioned along the exterior surface of the structural body 102A or cap 104A. In some embodiments, the tactile element 112 is representative of an actuator of a biased switch. For example, the tactile element 112 may be representative of the actuator of a normally-open (NO) switch that, when pressed, completes a circuit on a printed circuit board located in the cap 104A. Upon receiving an indication that the tactile element 112 has been pressed, the container 100A may infer that an action has been taken. For example, an individual may press the tactile element to activate the information display unit. As another example, an individual may be prompted to press the tactile element 112 to indicate that a dose of medication has been administered. As yet another example, an individual may be prompted to press the tactile element 112 as acknowledgement of a notification. As shown in FIG. 1A, the geometric center of the tactile element 112 may overlay the geometric center of the cap 104A. Here, for example, the midpoint of the substantially circular tactile element 112 overlays the midpoint of the substantially circular cap 104A. Since inadvertent interactions are more likely if the tactile element 112 is located along the side of the container 100A, the tactile element 112 may be located along the top surface of the cap 104A as shown in FIG. 1A.

Figure 2:
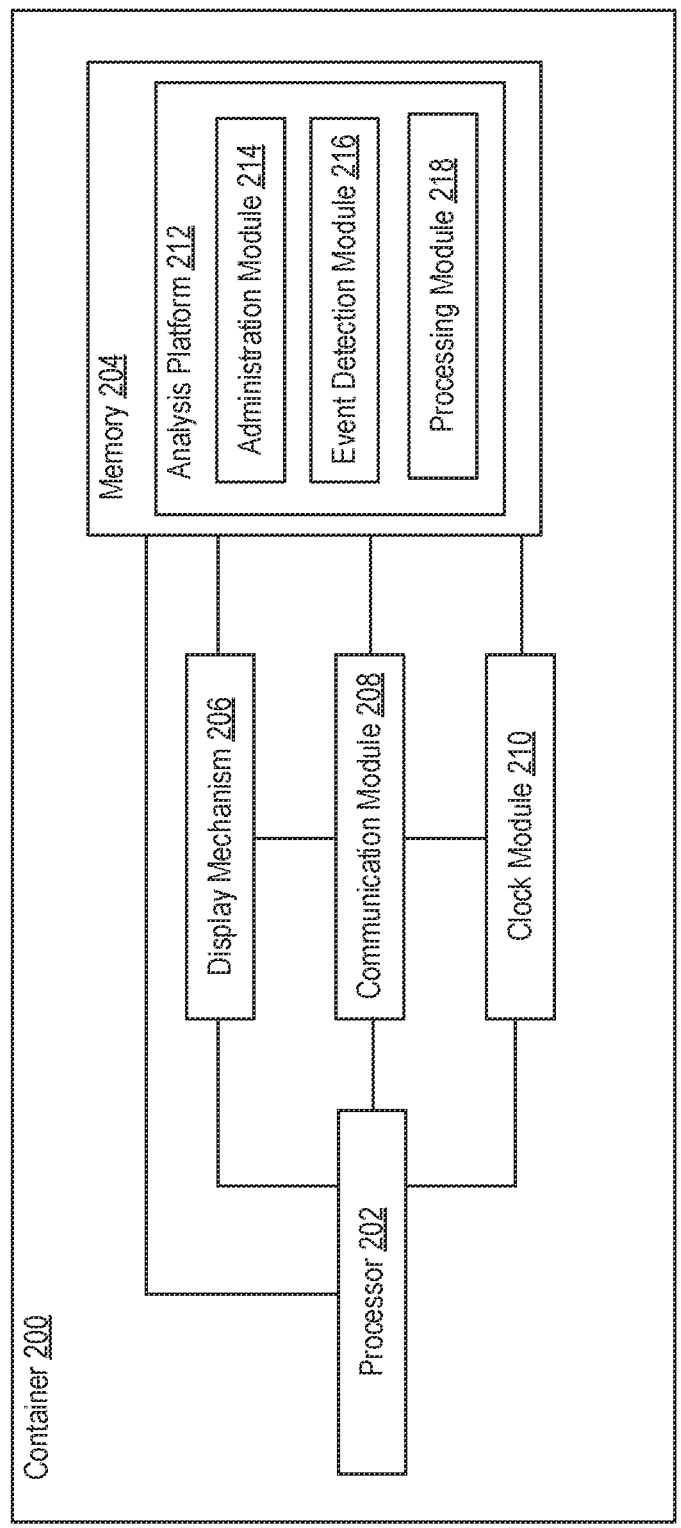
FIG. 2 illustrates an example of a container that is able to reliably assess whether an event related to an administration of medication has occurred.

FIG. 2 illustrates an example of a container 200 that is able to reliably assess whether an event related to an administration of medication has occurred. Here, the container 200 infers that medication has been administered based on events involving the cap. By cataloguing events experienced by the cap of the container 200, an analysis platform 212 can determine whether medication has been administered in compliance with a regimen. As further discussed below, other embodiments of the container 200 may infer that medication has been administered based on, for example, data generated by inertial measurement units (IMUs), pressure sensors, light sensors, tactile elements, and the like.

In some embodiments, the analysis platform 212 is embodied as a computer program that is executed by the container 200. In other embodiments, the analysis platform 212 is embodied as a computer program that is executed by a computing device to which the container 200 is communicatively connected. In such embodiments, the container 200 may transmit data regarding administrations of medication to the computing device for analysis by the computer program as further discussed below. Those skilled in the art will recognize that the computer program could also be distributed amongst the container 200 and computing device.

The container 200 can include a processor 202, memory 204, display mechanism 206, communication module 208, and clock module 210. The communication module 208 may be, for example, wireless communication circuitry designed to establish communication channels with computing devices. Examples of wireless communication circuitry include integrated circuits (also referred to as "chips") configured for Bluetooth, Wi-Fi®, ZigBee®, LoRa®, Near Field Communication (NFC), and the like. The processor 202 can have generic characteristics similar to general-purpose processors, or the processor 202 may be an application-specific integrated circuit (ASIC) that provides control functions to the container 200. As shown in FIG. 2, the processor 202 can be coupled to all components of the container 200, either directly or indirectly, for communication purposes.

The memory 204 may be comprised of any suitable type of storage medium, such as static random-access memory (SRAM), dynamic random-access memory (DRAM), electrically erasable programmable read-only memory (EEPROM), flash memory, or registers. In addition to storing instructions that can be executed by the processor 202, the memory 204 can also store data generated by the processor 202 (e.g., when executing the modules of the analysis platform 212). Note that the memory 204 is merely an abstract representation of a storage environment. The memory 204 could be comprised of actual memory chips or modules.

The communication module 208 can manage communications between the components of the container 200. The communication module 208 can also manage communications with other computing devices. For example, the analysis platform 212 may reside, partially or entirely, on a computing device to which the container 200 is communicatively connected as discussed above. Examples of computing devices include wearable electronic devices, mobile phones, tablet computers, and network-accessible server systems comprised of one or more servers. In such embodiments, the communication module 208 can transmit data generated by the container 200 to the computing device for further analysis by the analysis platform 212.

The clock module 210 is responsible for issuing a steady, high-frequency clock signal that can be used to determine whether a dose of medication is due to be administered. The clock module 210 may take the form of a chip that is mounted on the printed circuit board of the container 200.

For convenience, the analysis platform 212 may be referred to as a computer program that resides within the memory 204. However, the analysis platform 212 could be comprised of software, firmware, and/or hardware implemented in, or accessible to, the container 200. In accordance with embodiments described herein, the analysis platform 212 may include an administration module 214, event detection module 216, and processing module 218. These modules can be an integral part of the analysis platform 212. Alternatively, these modules can be logically separate from the analysis platform 212 but operate "alongside" it. Together, these modules may enable the analysis platform 212 to discover when administrations of medication are likely to have occurred.

The administration module 214 can be configured to examine a dosing schedule for the medication stored in the container 200 and then determine whether a dose is due to be administered based on a comparison of the dosing schedule and the clock signal generated by the clock module 210. More specifically, the administration module 214 can examine the dosing schedule to identify the times at which administration events are scheduled to occur and then determine, based on the clock signal, which administration events, if any, are due to be completed. In some embodiments the dosing schedule is stored in the memory 204, while in other embodiments the dosing schedule is stored in a remote memory accessible to the communication module 208 via a network.

If the administration module 214 determines that a dose of medication is due to be administered, the administration module 214 can cause a notification to be generated as an alert. More specifically, the administration module 214 can generate a signal for driving at least one indicator to produce the notification. Examples of indicators include speakers, feedback mechanisms, and display mechanisms. Thus, the container 200 may include a display mechanism 206 that is capable of visually conveying information. In some embodiments, the display mechanism 206 includes illuminant(s) that can be driven to emit light or change appearance on a periodic basis as a notification regarding what action, if any, should be taken with respect to the medication. Examples of illuminants include LEDs and organic LEDs. The components needed to operate the illuminant(s) may be connected to the illuminant(s) via conductive wires running through the container 200. Examples of operating components include drivers, processors (e.g., processor 202), and power sources such as batteries. While embodiments may be described in the context of illuminants, the technology is similarly applicable to other types of display mechanisms. For example, the container 200 may include reflective component(s) that create visual notifications by reflecting ambient light in addition to, or instead of, emissive components that create visual notifications by emitting light. Examples of reflective components include electrophoretic components and liquid crystal elements. Thus, the container 200 may include a display mechanism 206 that is configured to either emit or reflect light.

The event detection module 216 may be responsible for determining whether an event involving the cap of the container 200 has occurred based on signals generated by switch assemblies located inside the cap. These signals may indicate whether the switch assemblies have experienced a change in state. Since administration events normally require that the cap be removed from the structural body, the event detection module 216 may infer whether administration events have occurred based on the presence, frequency, or timing of the signals generated by the switch assemblies. Said another way, the event detection module 216 may record that an administration event has occurred responsive to discovering that the switch assemblies experienced a change in state since changes in state are generally indicative of administration events. In other embodiments, the event detection module 216 may infer whether administration events occurred based on an analysis of movement data generated by an IMU that includes an accelerometer, gyroscope, etc. In other embodiments, the event detection module 216 may infer whether administration events occurred based on an analysis of tactile data representative of interactions with a tactile element of the container 200. For example, the event detection module 216 may be programmed to infer that interactions with a tactile element (e.g., tactile element 112 of FIG. 1A) are representative of confirmations that administration events took place.

The processing module 214 may be responsible for applying operations to data obtained by the analysis platform 212. The container 200 may produce data over time that indicates when doses of medication were administered. The processing module 214 may process (e.g., denoise, filter, or otherwise alter) this data so that it is usable by the other modules of the analysis platform 212. Additionally or alternatively, the processing module 214 may be responsible for determining whether further action is necessary before this data is transmitted to a computing device by the communication module 208. For example, the processing module 214 may assign priority measures to the data so that if bandwidth or power is limited, only the data deemed to be high priority is transmitted to the computing device. As further discussed below, these priority measures may also be useful in determining an order in which to send the data to the computing device. As another example, the processing module 214 may filter the data to ensure that only relevant data (e.g., data concerning administrations of medication) is transmitted to the computing device.

Figure 3:
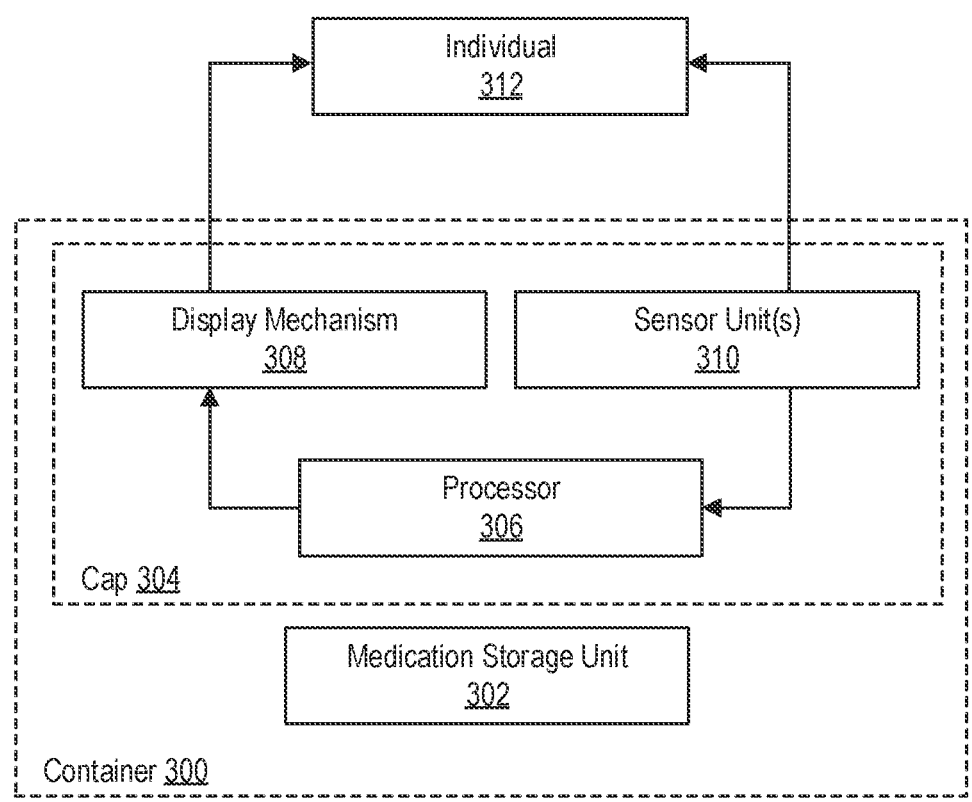
FIG. 3 includes a high-level system-level diagram of an embodiment of a container in which the processor, display mechanism, and sensor unit(s) are housed within the cap.

FIG. 3 includes a high-level system-level diagram of an embodiment of a container 300 in which the processor 306, display mechanism 308, and sensor unit(s) 310 are housed within the cap 304. One example of a sensor unit 310 is a switch assembly configured to generate signals from which occurrences of events involving the cap 304 can be inferred. Other examples of sensor units 310 include IMUs, pressure sensors, tactile elements, and the like.

In some embodiments, the display mechanism 308 includes a plurality of LEDs that, when driven by the processor 306, convey information regarding the time that has elapsed since the cap 304 was last removed and/or the time until the cap 304 should be next removed. Alternatively, the plurality of LEDs may convey information regarding the number of doses of medication remaining in the medication storage unit 302. In such embodiments, all of the LEDs may initially be driven by the processor 306. Then, as doses are administered by the individual 312, the LEDs may be sequentially turned off to visually indicate when more medication will be needed.

In some embodiments, the display mechanism 308 includes a plurality of independently operable displays capable of presenting different types of information. For instance, a first display may include a digital clock while a second display element may include information regarding the medication or container 300. As an example, the second display element may display the name of the medication or a color associated with the medication (e.g., on its packaging) to give the individual 312 confidence that the container 300 (and, more specifically, the dosing schedule implemented by the container 300) has been correctly matched with the medication stored therein. As another example, the second display element may display status indicators related to the container 300, such as power level, connectivity status, and the like.

In some embodiments, the display mechanism 308 is an "always on" display element capable of visually conveying information on a continual basis. One drawback of this approach, however, is that such display mechanisms may consume significant amounts of power over long intervals of time. One option for addressing this drawback is to ensure that the display mechanism 308 is only driven by the processor 306 when the individual 312 is nearby. The individual 312 may be, for example, the person to whom the medication has been prescribed or another person responsible for assisting in administering the medication. The processor 306 may be able to establish proximity of the individual 312 in several different ways.

For example, the container 300 may include a microphone configured to generate data indicative of sounds external to its structural body. In such embodiments, the processor 306 may drive the display mechanism 308 only upon inferring, based on data generated by the microphone, that the individual 312 is likely within a given proximity. The inference may be based on the presence of a sound that is representative of the individual 312. For instance, the processor 306 may be able to detect keywords in the data, or the processor 306 may be able to identify an audible characteristic (e.g., frequency or cadence) that is representative of the individual 312.

As another example, the container 300 may include a proximity sensor configured to generate data representative of a series of proximity measurements indicative of proximity of the individual 312. The proximity sensor may emit an electromagnetic field or a beam of electromagnetic radiation (e.g., infrared radiation) and then look for changes in the electromagnetic field or return beam of electromagnetic radiation. In such embodiments, the processor 306 may drive the display mechanism 308 only upon inferring, based on the data, that the individual 312 is within a given proximity.

As another example, the container 300 may include an accelerometer configured to generate data representative of a series of measurements of acceleration of the container 300. In such embodiments, the processor 306 may drive the display mechanism 308 only upon inferring, based on the data, that the individual 312 has interacted with the container 300 within a given amount of time. The inference may be based on at least one acceleration measurement that exceeds a predetermined value or a series of acceleration measurements that match a pattern-defining parameter.

As another example, the container 300 may include a tactile element (e.g., tactile element 112 of FIG. 1A) that is accessible through its durable housing. Data indicative of events involving interactions with the tactile element can be generated by, for example, a pressure sensor or electrical contact positioned beneath the tactile element. In such embodiments, the processor 306 may drive the display mechanism 308 only upon determining, based on the data, that the individual 312 has interacted with the tactile element within a given amount of time.

As another example, the container 300 may include a communication module configured to communicate with a computing device associated with the individual 312. For instance, the container 300 may include a Bluetooth Low Energy (BLE) chipset or a Wi-Fi chipset. In such embodiments, the processor 306 may drive the display mechanism 308 only upon inferring that the patient 312 is within a given proximity. Such an inference may be based on whether the communication module is presently able to establish a communication channel with the computing device.

While the examples provided above concern controlling the display mechanism 308 in a less power-intensive manner, similar approaches may be employed to intelligently drive or manage other components of the container 300. For example, to conserve power, the processor 306 may activate sensors (e.g., infrared sensors, acoustic sensors, accelerometers, gyroscopes) housed in the container 300 only upon inferring that the individual 312 is nearby.

Overview of Communication Environment

Figure 4:
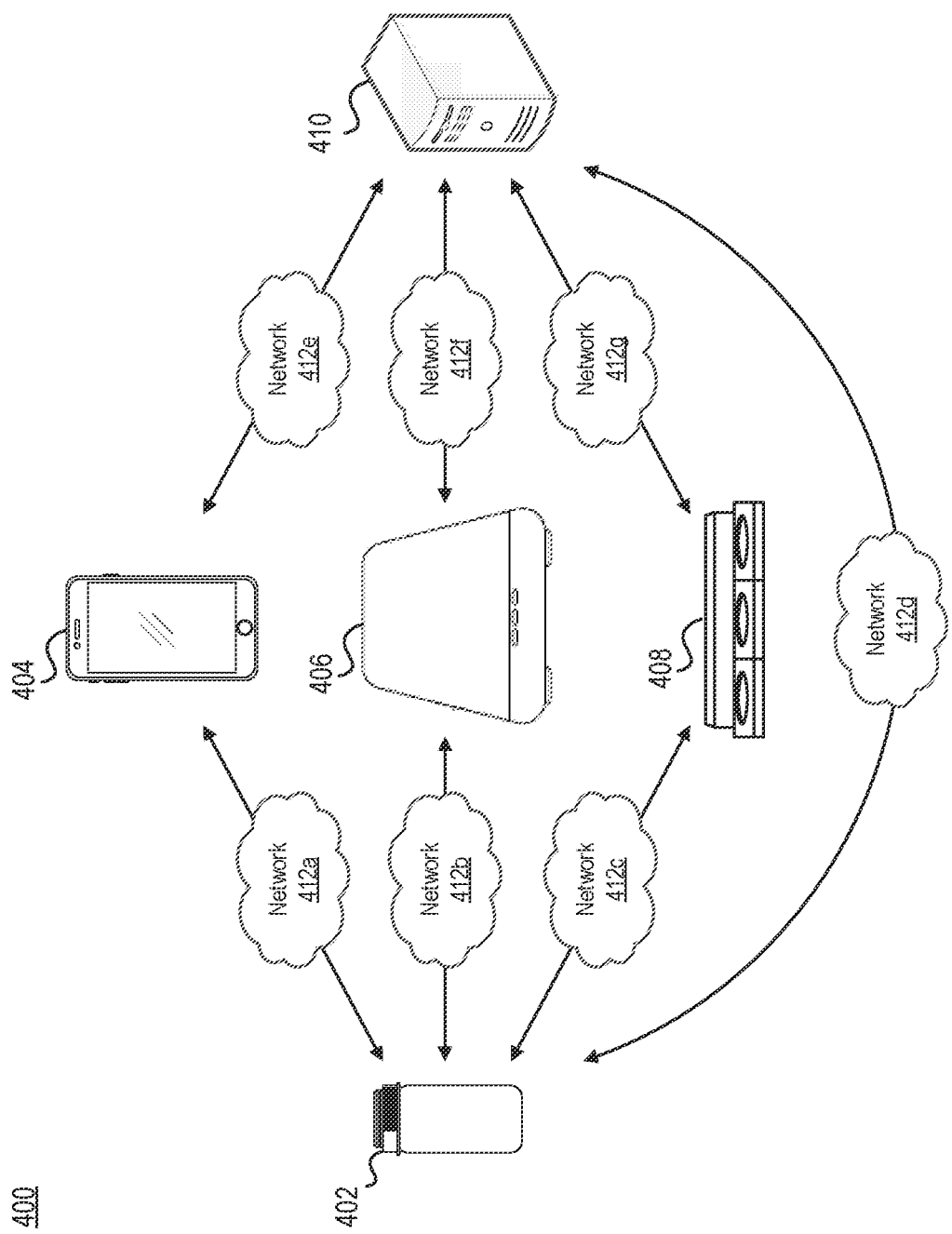
FIG. 4 depicts an example of a communication environment that includes a container having medication stored therein.

FIG. 4 depicts an example of a communication environment 400 that includes a container 402 having medication stored therein. As discussed above, the container 402 may be able to communicate with one or more computing devices. For example, the container 402 may transmit data related to administrations of the medication to a computing device for further analysis. Examples of computing devices include mobile phones 404, hub units 406, docking units 408, and computer servers 410. The container 402 and computing device(s) may collectively be referred to as the "networked devices."

The networked devices can be connected to one another via one or more networks 412*a-g*. The network(s) 412*a-g* can include personal area networks (PANs), local area networks (LANs), wide area networks (WANs), metropolitan area networks (MANs), cellular networks, the Internet, etc. Additionally or alternatively, the networked devices may communicate with one another over a short-range communication protocol, such as Bluetooth, NFC, Wi-Fi, ZigBee, LoRa, another commercial point-to-point protocol, or a proprietary point-to-point protocol. For example, the container 402 may include a BLE chipset or a Wi-Fi chipset that establishes a wireless communication channel with the mobile phone 404, which may be communicatively coupled to the computer server 410 via a Wi-Fi communication channel or a cellular communication channel.

Embodiments of the communication environment 400 may include some or all of the networked devices. For example, some embodiments of the communication environment 400 include the container 402 and a single computing device (e.g., the mobile phone 404) that is responsible for analyzing data generated by the container 402. As another example, some embodiments of the communication environment 400 include the container 402 and a computer server 410 on which data generated by the container 402 is stored for subsequent analysis. Further information on networked containers can be found in U.S. Provisional Application No. 62/962,784, titled "Networked Containers Designed to Promote Compliance with a Medication Regimen," which is incorporated by reference herein in its entirety.

Figure 5:
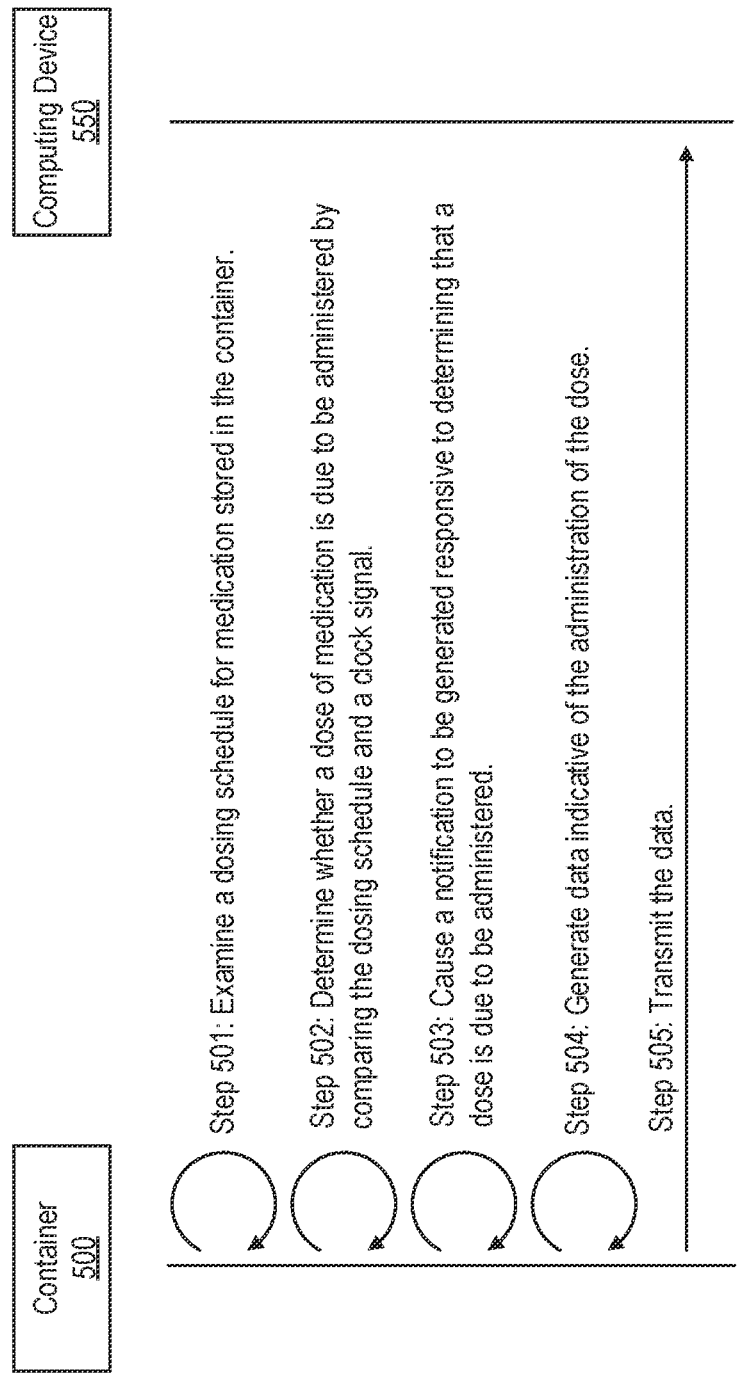
FIG. 5 includes a high-level illustration of communications between a container that includes a bulk supply of medication and a computing device that is responsible for processing, examining, or forwarding data related to administrations of the medication so that compliance with a regimen can be determined.

FIG. 5 includes a high-level illustration of communications between a container 500 that includes a bulk supply of medication and a computing device 550 that is responsible for processing, examining, or forwarding data related to administrations of the medication so that compliance with a regimen can be determined. One example of a computing device 550 is a mobile phone that is associated with the person to whom the medication has been prescribed.

Initially, the container 500 can examine a dosing schedule for a medication stored therein (step 501). In some embodiments, the dosing schedule is manually loaded into local memory. For example, a medical professional or the person to whom the medication has been prescribed may input the dosing schedule through a computer program executing on the computing device 550, and the computer program may forward the dosing schedule to the container 500. In other embodiments, the dosing schedule is automatically retrieved from a remote memory during a configuration process. For example, the dosing schedule may be retrieved from a network-accessible storage medium associated with a medical enterprise such as a hospital or pharmacy when the medication is loaded into the container 500.

Then, the container 500 can determine whether a dose of medication is due to be administered by comparing the dosing schedule and a clock signal generated by a clock module (step 502). In response to determining that a dose of medication is due to be administered, the container 500 can cause a notification to be generated by an indicator (step 503). Examples of indicators include illuminants operable to produce visual notifications, speakers operable to produce audible notifications, and feedback mechanisms operable to produce tactile notifications. In some embodiments, the notification is generated on a periodic basis. For example, the container 500 may drive an illuminant such that light is emitted (e.g., by flashing or pulsing) on a periodic basis as a visual notification.

The container 500 may be able to generate data indicative of administrations of doses of medication (step 504). This administration data may be useful in determining the degree of compliance with a regimen requiring administration of the medication. For example, the administration data may provide insights into the compliance of individual administration events (e.g., whether a scheduled dose was skipped) or series of administration events (e.g., whether scheduled doses are routinely administered late).

This administration data may comprise, or be derived from, various types of data generated by components of the container 500. For example, the container 500 may infer that administration events have occurred based on an analysis of signals generated by switch assemblies contained within the cap. As another example, the container 500 may infer that administration events have occurred based on an analysis of data generated by an IMU whose movement is representative of movement of the container 500. As another example, the container 500 may infer that administration events have occurred based on an analysis of data generated by a pressure sensor located beneath the cavity in which medication is stored. As another example, the container 500 may infer that administration events have occurred based on an analysis of data representative of interactions with a tactile element accessible along the outer surface of the container 500.

The container 500 may transmit at least some of the administration data to the computing device 500 for analysis (step 505). For example, a processor responsible for processing the administration data may forward this data to a transmitter for modulation onto an antenna for wireless transmission to the computing device 550. The transmitter may be part of a transceiver capable of transmitting communications to, and receiving communications from, the computing device 550. Step 505 may be performed whenever the container 500 and computing device 550 are communicatively connected to one another. For example, if the container 500 and computing device 550 are configured to communicate with one another via a short-range communication protocol, step 505 may be performed whenever the computing device 550 is within sufficient proximity of the container 500 to communicate via the short-range communication protocol.

Other steps could also be performed by the container 500 and/or computing device 550. For example, the computing device 550 may be responsible for transmitting information regarding the regimen to the container 500 for implementation. Said another way, the computing device 550 may transmit information regarding when doses are to be administered to the container 500, and then the container 500 may store this information for use in determining when doses are due to be administered.

Note that, in some embodiments, the container 500 may be designed in such a manner to ensure the cap has been placed on the corresponding structural body. As one example, the cap and corresponding structural body may be color coded as a matching set. Thus, the cap and corresponding structural body may have a given color affixed thereto to indicate the relationship. As another example, the cap and corresponding structural body may be pattern coded as a matching set. For instance, the cap and corresponding structural body may have matching patterns imprinted thereon to indicate the relationship.

Figure 6:
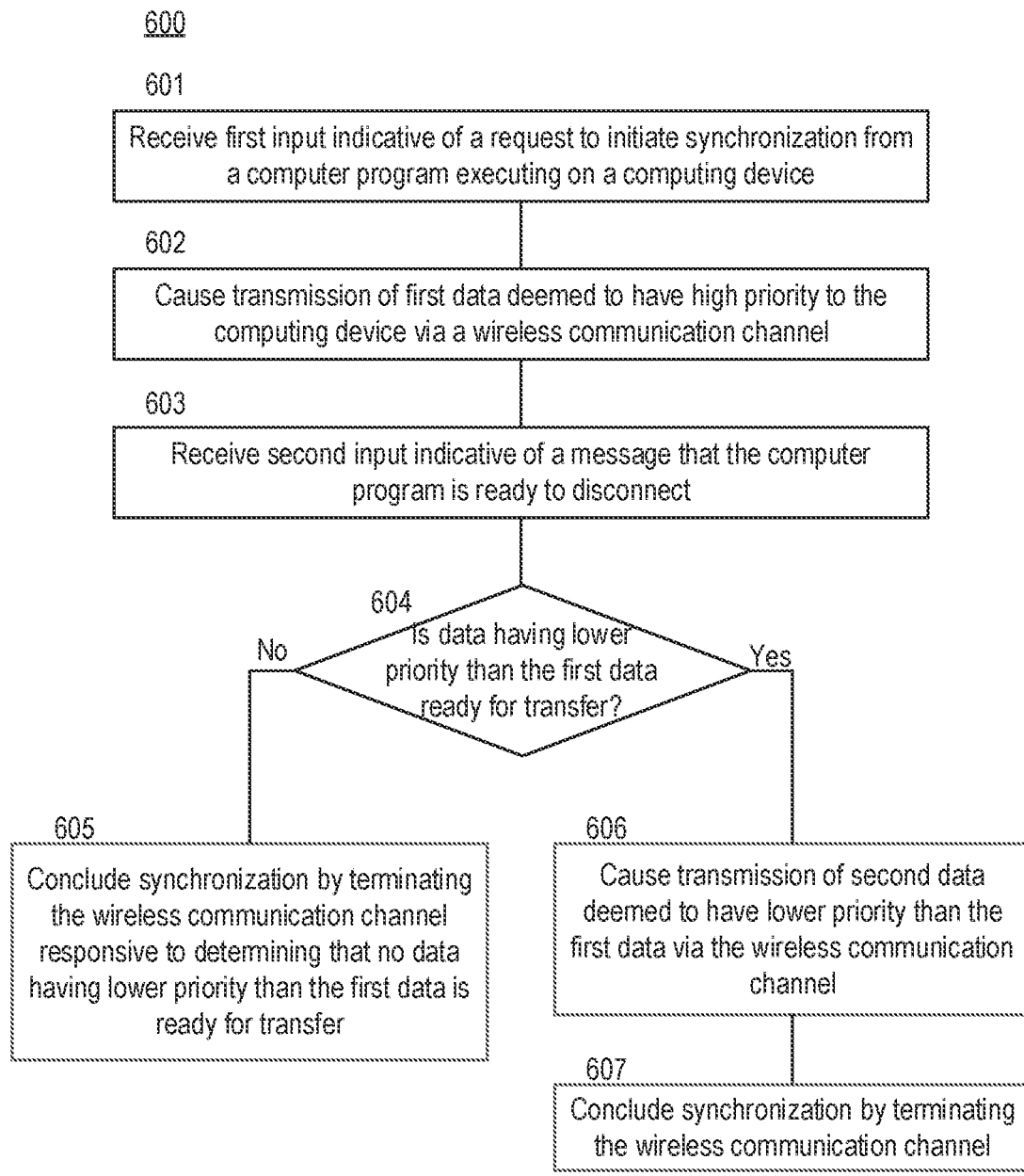
FIG. 6 includes a flow diagram of a process for implementing an automated process (also referred to as a "handshake") for transferring data between a container and a computer program executing on a computing device in a more efficient manner.

FIG. 6 includes a flow diagram of a process 600 for implementing an automated process (also referred to as a "handshake") for transferring data between a container and a computer program executing on a computing device in a more efficient manner. Generally, data is transferred between the container and computer program through a request-response pattern in which the computer program sends a request message to the container and the container responds with a response message. Because the amount of power available to the container is limited, it may be desirable to limit the number of exchanges (also referred to as "synchronization events" or "synchronization sessions") that occur.

Some data that is generated by the container may be low priority. Low-priority data may be data that is unrelated to administrations of medication (e.g., data related to diagnostics or status), or spurious enough that the data need not be requested during every synchronization (e.g., data related to errors, such as those experienced by the switch assemblies). One example of low-priority data is data related to false triggers. Since this low-priority data is not needed to establish whether medication was administered in accordance with a regimen, it can be transmitted to the computer program less frequently. Accordingly, rather than the computer program requesting the same type(s) of data during each synchronization event, the computer program may instead request that any high-priority data generated since the previous synchronization event be transmitted and then send a confirmation message indicating that it is ready to disconnect. The container can send low-priority data upon receiving the confirmation message, or the container can simply disconnect if there is no low-priority data to send. Performing this final handshake during each synchronization event enables power to be saved where there is no low-priority data to send.

As shown in FIG. 6, the container may initially receive first input indicative of a request to initiate synchronization from a computer program executing on a computing device (step 601). The computer program may be designed to promote adherence to a dosing schedule for medication stored in the container. For example, the computer program may be configured to analyze data regarding administrations of medication that was generated by the container to determine whether the medication was administered in accordance with a dosing schedule. Similarly, the computer program may be configured to analyze data regarding administrations of medication to establish how much medication resides in the container. In some embodiments requests to initiate synchronization are received from the computer program on a periodic basis, while in other embodiments requests to initiate synchronization are received from the computer program on an ad hoc basis. For example, the computer program may transmit a request to initiate synchronization whenever communication with the container is possible over a short-range communication protocol. Thus, requests to initiate synchronization may be transmitted by the computer program whenever the container and computing device are within proximity of one another.

Alternatively, the container may be responsible for determining when synchronization with the computer program can occur. For example, the container may be configured to locally broadcast signals in accordance with a short-range communication protocol to determine whether synchronization can occur. One example of a short-range communication protocol over which synchronization can be performed is Bluetooth. These signals may be representative of advertising signals that are broadcast periodically (e.g., every 60 minutes, 90 minutes, or 120 minutes) or on an ad hoc basis (e.g., whenever an event occurs). Thus, the computer program may only send a request to initiate synchronization responsive to receiving an advertising signal from the container.

Thereafter, the container may cause transmission of first data deemed to have high priority to the computing device via a wireless communication channel (step 602). Priority may be determined based on priority measures assigned different types of data by the computer program. For example, the computer program may indicate that data regarding administrations of medication (also referred to as "administration data") is high priority while data regarding status (e.g., power level, connectivity state, and amount of remaining medication) is lower priority.

As discussed above, the container can then receive a second input indicative of a message that the computer program is ready to disconnect (step 603). This second input may be representative of a request to complete synchronization by terminating the wireless communication channel established between the container and computing device. Upon receiving the second input, the container can determine whether data having lower priority than the first data is ready for transfer (step 604). In some instances, the container will determine that no data having lower priority than the first data is ready for transfer, and the container can simply conclude synchronization by terminating the wireless communication channel (step 605). In other instances, the container will determine that data having lower priority than the first data is ready for transfer. In such instances, the container can cause transmission of second data having lower priority than the first data (step 606) and then conclude synchronization by terminating the wireless communication channel (step 607).

Those skilled in the art will recognize that the process 600 will differ depending on whether low-priority data is ready for transfer. Over an extended period of time (e.g., several hours or days), the computer program may transmit a series of requests to initiate synchronization to the container. Some exchanges may conclude following transmission of high-priority data, while other exchanges may conclude following transmission of high- and low-priority data. Each of these exchanges may occur over a separate instance of a wireless communication channel established in accordance with a short-range communication protocol.

To secure data prior to transmission to the computer program, the container may implement an encryption scheme. Some encryption schemes provide for an initial pairing of the container and computer program using a shared code or password and then involve a power-intensive sequence of exchanges and cryptographic computations. To lessen the amount of power that is consumed over time, the container may instead use a master key that is stored during the initial pairing to restore communications with the computer program during subsequent synchronization events. Such an approach enables the container to quickly initiate a secure connection with the computer program in a manner that requires fewer exchanges and cryptographic computations (and thus less power).

Figure 7:
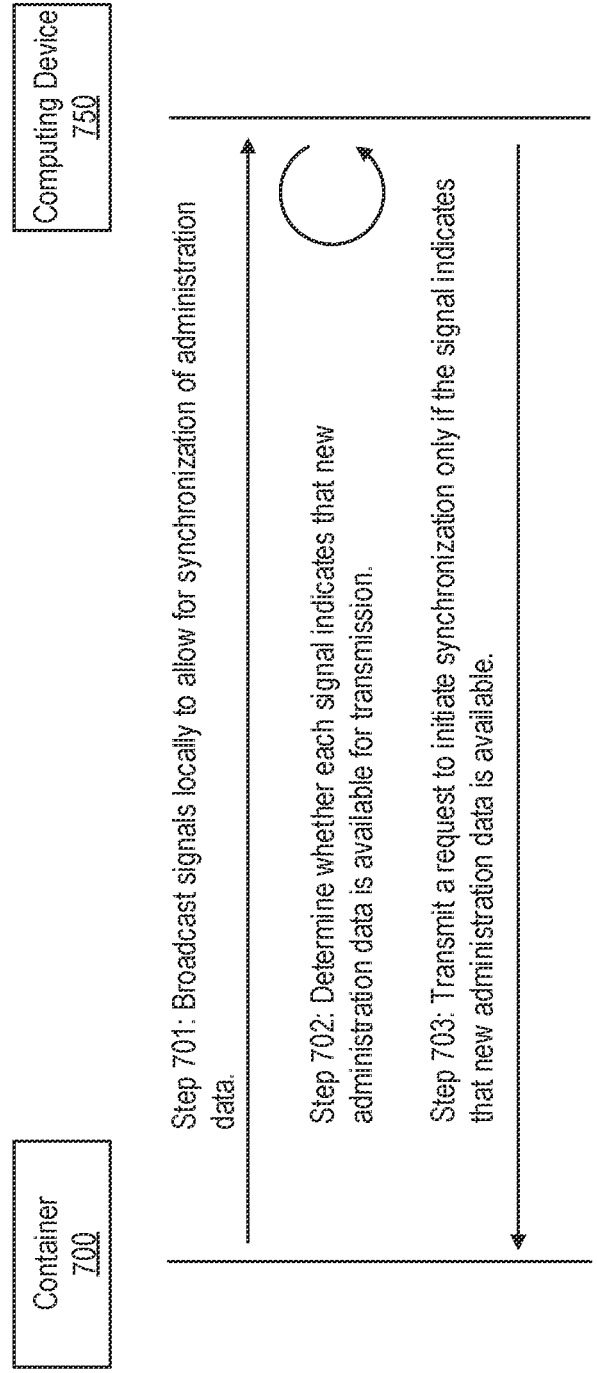
FIG. 7 includes a flow diagram of a process for performing an abbreviated synchronization event to conserve power.

FIG. 7 includes a flow diagram of a process for performing an abbreviated synchronization event to conserve power. As discussed above, a container 700 may be configured to transmit data regarding administrations of medication to a computing device 750 for further analysis. Generally, administration data is periodically transmitted from the container 700 to the computing device 750 as part of a synchronization event. Because each synchronization event involves an exchange of messages between the container 700 and computing device 750, completing the synchronization event will require that power be consumed by the container 700 and computing device 750. By implementing the process of FIG. 7, however, synchronization events can be avoided when the container 700 does not have new administration data available for transmission to the computing device 750.

Over time, the container 700 may locally broadcast signals to allow for synchronization of administration data stored thereon (step 701). These signals may be broadcast periodically (e.g., once every 15 minutes, 30 minutes, or 60 minutes) regardless of whether there is new data to be transmitted to the computing device 750 or whether the computing device 750 is presently within proximity of the container 700. Generally, these signals are broadcast by the container 700 in accordance with a short-range communication protocol. For example, these signals may be representative of advertising signals that are broadcast by the container 700 over Bluetooth.

To reduce the number of unnecessary synchronization events, the container 700 may place a label (also referred to as a "flag") in each signal that indicates whether new administration data has been generated since the most recent transfer of administration data to the computing device 750. Accordingly, for each signal that is received, the computing device 750 may determine whether the signal indicates that new administration data is available for transmission from the container 700 (step 702). More specifically, the computing device 750 may parse each signal to discover whether a flag is present that indicates new administration data is available. The computing device 750 may transmit a request to initiate synchronization only if the signal indicates that new administration data is available (step 703). Accordingly, the computing device 750 may choose to initiate synchronization only when new administration data is available, thereby allowing the container 700 and computing device 750 to save power that would be required to complete synchronization. Note, however, that the computing device 750 may register that a synchronization event occurred whenever a signal is received. Thus, the computing device 750 may register that a synchronization event occurred regardless of whether new administration data was actually obtained from the container 700.

In some embodiments, the flag only indicates whether new high-priority data is available. For example, the flag may be used to indicate whether high-priority data such as administration data has been generated since the most recent synchronization event. In other embodiments, the flag indicates whether new high- or low-priority data is available. As discussed above, priority may be based on priority measures assigned different types of data by an analysis platform executing on the container 700 and/or computing device

750. If all of the new data is low priority, then the computing device 750 may opt against a transfer of such data until new high-priority data is available.

Alternatively, the container 700 may be configured to not broadcast any signals unless new administration data is available. Such an approach will cause even less power to be consumed than the process of FIG. 7, though it may come at the expense of the computing device 750 losing the ability to establish whether the container 700 is within range. For example, the signals broadcast by the container 700 may also include information regarding its state, such as power level and connectivity status, in addition to the flag. If the signals are not broadcast unless new data is available, the computing device 750 may have little insight into the status of the container 700.

Approaches to Increasing Robustness of Wireless Communications

As discussed above, a container may transmit data regarding administrations of the medication stored therein to a computing device for analysis. For example, a container may transmit data to a mobile phone on which a mobile application is executing, and the mobile application may be responsible for determining, by examining the data, whether the medication is being administered in compliance with a regimen. However, this may not be possible when the mobile phone is not proximate to the container. Assume, for example, that an individual leaves her home immediately after administering the medication. In such a scenario, a wireless communication channel established between the mobile phone and container will be disrupted. Monitoring adherence is difficult, if not impossible, if the data generated by the container fails to reach the mobile phone in a reliable manner. Introduced here, therefore, are two approaches for improving the reliability and robustness of wireless connections established in accordance with short-range communication protocols.

A. Synchronization Scheme Robust to Intermittent Connections

The first approach involves implementing a synchronization scheme that is robust to intermittent connections. A container may generate data over time that is related to administrations of the medication stored therein. To determine whether the medication is being administered in compliance with a regimen, a computer program that is executing on a computing device may request that the data be downloaded from the container. The computer program may be representative of an analysis platform that is programmed to promote adherence to the regimen, for example, by generating reminders, offering support, and the like. The data may be transferred from the container to the computer program through a request-response pattern as discussed above with reference to FIG. 6. Oftentimes, multiple response messages are required in order to send all of the data to the computing device. However, this can be problematic if the connection between the container and computing device is inconsistent as some of the data may be inadvertently lost. Moreover, because the data is normally transferred in a manner that is ambivalent to priority (e.g., from oldest to newest, or vice versa), the importance of the lost data may be difficult, if not impossible, to determine. The scheme described below addresses these concerns by coordinating the transfer of data from the container to the computing device such that a smaller amount of data is transferred during the initial synchronization event. After each successful synchronization event, the payload size can be increased so that larger amounts of data are transferred to the computing device.

FIG. 8 includes a flow diagram of a process 800 for transferring data from a container in which medication is stored to a computing device. Initially, a container can broadcast a signal to indicate willingness to perform synchronization (step 801). This signal may be one of multiple signals broadcast by the container on a periodic basis. For example, the container may be configured to periodically broadcast a signal over a wireless PAN (e.g., Bluetooth) so as to advertise its presence to nearby computing devices.

Thereafter, the container may receive first input indicative of a response to the signal from a computer program that is executing on a computing device (step 802). The computer program may be designed to monitor adherence to a regimen that requires administrations of the medication that is stored in the container. Generally, the computing device is associated with the individual to whom the medication has been prescribed. However, the computing device could be associated with another person, such as a medical professional or caregiver responsible for providing care to the individual.

In some embodiments, the container is configured to determine what data, if any, is available for transmittal to the computing device upon receiving the first input. For example, the container may discover that high- and low-priority data is available for transmission to the computing device, or the container may discover that only high- or low-priority data is available for transmission to the computing device. These priority levels may be determined based on priority measures assigned to different types of data by the computer program. For example, if the container determines that data of different priority levels is available for transmittal to the computing device, the container may parse the data into a series of datasets and then sort those datasets in order of priority prior to inclusion in the respective payloads of messages destined for the computing device.

The container can then cause wireless transmission of a series of messages whose respective payloads contain the data to the computing device. These messages may be transmitted in order of increasing payload size and/or decreasing payload priority. Thus, the container may cause wireless transmission of a first message whose payload is a first size to the computing device (step 803). Then, upon receiving second input indicative of an acknowledgement that the first message was received by the computer program (step 804), the container may cause wireless transmission of a second message whose payload is a second size larger than the first size to the computing device (step 805). As mentioned above, the data contained in the first message may also be higher priority than the data contained in the second message. Increasing payload size (and, in some embodiments, decreasing, payload priority) after each successful synchronization event ensures that the computer program obtains the most important information relatively quickly.

Generally, the amount of data included in each message is measured in terms of the number of administrations. So a "small message" may only include data related one or two administrations of medication while a "large message" may include data related to eight or more administrations of medication. In some embodiments, the size of the payload increases linearly up to a threshold value. In other embodiments, the size of the payload increases exponentially up to a threshold value.

FIG. 9 includes a flow diagram of a process 900 for acquiring data from a container in which medication is stored. In this embodiment, the process 900 is performed by a computing device that includes the necessary software, firmware, or hardware for initiating and then maintaining a wireless communication channel over which data can be transferred from the container. Examples of computing devices include wearable electronic devices, mobile phones, tablet computers, and the like.

Initially, a computing device will discover a signal that is locally broadcast by a container that has medication stored therein (step 901). As mentioned above, this signal may be one of multiple signals broadcast by the container so as to advertise its presence. The computing device can then determine that the signal indicates data is available for download from the container (step 902). For example, the computing device may parse the signal to discover whether a flag is present that indicates data has been generated since the most recent transmission of data to the computing device by the container.

The computing device can then initiate a wireless communication channel over which the data can be acquired from the container (step 903). In some embodiments, this wireless communication channel operates as a unidirectional channel over which data can only be transferred from the container to the computing device. In other embodiments, this wireless communication channel operates as a bidirectional channel over which data can be transferred from the container to the computing device and vice versa. The wireless communication channel may be established in accordance with a short-range communication protocol, such as Bluetooth, NFC, Wi-Fi, ZigBee, LoRa, and the like.

Thereafter, the computing device can receive, via the wireless communication channel, a plurality of messages from the container that contain the data in corresponding payloads (step 904). The plurality of messages may be transmitted to the computing device by the container in order of increasing payload size and/or decreasing payload priority. At a high level, the priority of each payload may correspond to the priority of the data contained therein. Thus, messages that contain data regarding administrations of medication may be higher priority than, and thus transmitted before, messages that contain data regarding status of the container. Moreover, messages that contain data regarding more recent administrations of medication may be higher priority than, and thus transmitted before, messages that contain data regarding less recent administrations of medication. In some embodiments, each message includes a flag that indicates whether the data contained in the corresponding payload is deemed to have high or low priority to the computing device (and, more specifically, to a computer program executing on the computing device).

Note that other steps could also be performed by the container and computing device. Assume, for example, that the container receives input indicative of a request from the computing device to initiate a transfer of data stored thereon. The container may forward the data to, for example, a BLE chipset for transmission to the computing device as a plurality of messages. If the container determines that the wireless communication channel established by the BLE chipset was lost and then regained, then the container may resume forwarding the data to the BLE chipset. However, the size of payloads may be reduced. For example, the container may lessen the payload size to match the last message that was confirmed as being received by the computing device. As another example, the container may reset the payload size to a minimum size that is programmed in the container or the computer program executing in the computing device. Thus, the first message that is sent upon reinitiating the wireless communication channel may have the same payload size as the initial message sent as part of the synchronization event.

This approach ensures that the most important data, which may be critical to making informed decisions about individuals' health, is reliably transferred from containers to computing devices for analysis. At a high level, it is beneficial to opportunistically prioritize sending important data as soon as a wireless communication channel is established so as to ensure that this data is transferred in a timely manner. If the wireless communication channel is disrupted, the data that will be lost or not transferred is more likely to be low-priority data (and thus will have less of an impact).

B. Wrapper Function for More Reliable Wireless Connections

The second approach involves employing a wrapper function (or simply "wrapper") to improve the reliability of connections established in accordance with short-range communication protocols. Assume, for example, that a container is programmed to transfer data related to administrations of medication to a computing device over Bluetooth. It is important that the container is able to reliably connect to a computer program executing on the computing device in the background so that data received from the container is up to date. While the computer program will generally not be open at the time of synchronization, it is important that the computer program obtain data from the container in near real time to have a full understanding of whether the medication is being administered appropriately. It is easy for the wireless communication channel between the container and computing device to be disrupted, however. As further discussed below, the wrapper addresses this issue by employing a state tracking scheme to resolve intermittent connectivity.

At a high level, the wrapper-when implemented by the computer program-provides another layer of state tracking on top of the operating system. Normally, a series of requests are made to the operating system to initiate a wireless communication channel over Bluetooth. Each of these requests represents an opportunity for failure, however. The approaches described below allow these requests to be circumvented in some situations, thereby improving reliability.

Figure 10:
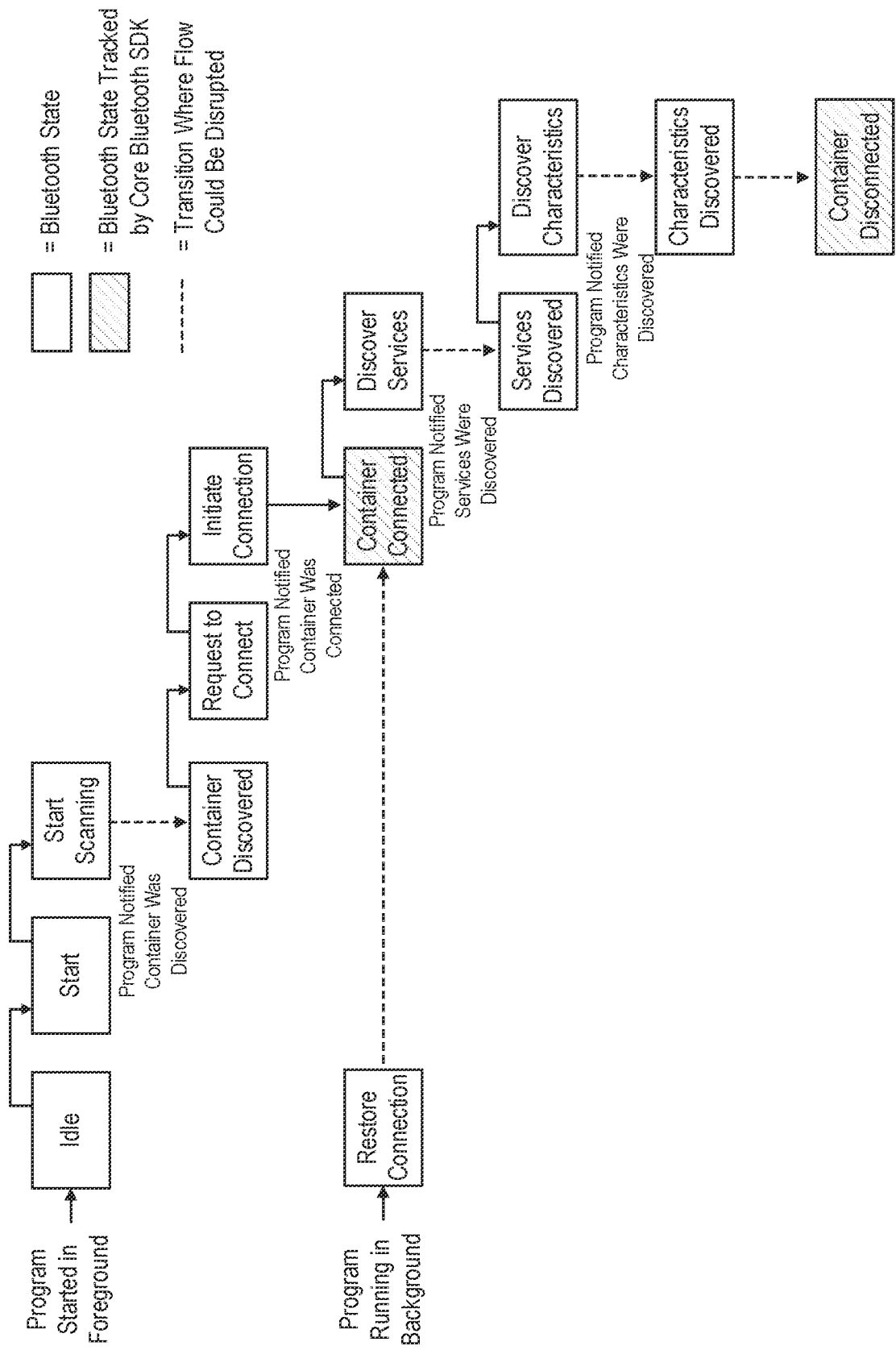
FIG. 10 includes a high-level illustration of a conventional pairing process by which a container could be communicatively connected to a computing device via Bluetooth for the purpose of transferring data stored thereon.

FIG. 10 includes a high-level illustration of a conventional pairing process by which a container could be communicatively connected to a computing device via Bluetooth for the purpose of transferring data stored thereon. Initially, an individual will initiate or start a computer program that executes in the foreground of the computing device. Then, the individual can begin a scanning process in which nearby Bluetooth-enabled devices are discovered. Upon discovering the container, the computing device will notify the computer program.

Thereafter, the computing device can request to connect to the container. For example, the computing device may transmit a request to the container with the intention of provoking a response. Assuming that the container indicates a willingness to connect, the computing device will connect to the container. The computing device will notify the computer program upon initiating a connection with the container. After this pairing process is completed, the container may seek to transfer data to the computer program as it is executed by the computing device in the background. The computing device can then attempt to discover which services, if any, are available on the container. Similarly, the computing device can attempt to discover characteristics of the container. As services and characteristics are discovered, the computing device may notify the computer program.

In order for connections to be established over Bluetooth, the computing device will execute a computer program that utilizes services provided by an SDK (or API) in order to manage those connections. The SDK is typically made available by the manufacturer of the operating system. If, for example, the computing device is an iPhone® mobile digital device manufactured by Apple Inc., then the Bluetooth SDK that is available to use with its operating system (i.e., iOS) tracks two states. The first state indicates when the container is connected to the computing device, and the second state indicates when the container is disconnected from the computing device. As shown in FIG. 10, there are several transitions where the connection between the container and computing device could be broken, however. Because only two states are actively tracked, these transitions can pose significant issues. For example, broken connections (also referred to as "dropped connections") may lead to errors in transferring data if not properly and promptly identified.

During the process of forming a connection over Bluetooth, there will be several occurrences of a computer program making calls to the lower-level Bluetooth functionality provided by the Bluetooth SDK or API (also referred to as the "Bluetooth stack") implemented by the operating system of the computing device on which the computer program executes. These steps are shown and described with respect to FIGS. 11-14. In general, these steps include: (i) initiating BLE scanning, (ii) requesting a connection upon discovery of a peripheral (e.g., a container), (iii) requesting available services upon establishing a connection, (iv) requesting available characteristics of the peripheral, (v) exchanging program-level data, (vi) requesting a disconnection from the peripheral, and (vii) requesting a reconnection with the peripheral, if necessary. For each of these requests of the underlying Bluetooth stack, there is some amount of time that the computer program is waiting for a response, and the response could signal either a success or failure of that particular request. State can be tracked by, for each request of the underlying Bluetooth stack, having the computer program record that the request has been made. As further discussed below with reference to FIG. 12, the state can be updated upon receiving a response from the underlying Bluetooth stack. By keeping track of the state, the computer program can better recover from potential failure. For example, if characteristic discovery for a peripheral fails, then characteristic discovery can simply be requested again (e.g., up to N times) rather than completely sever the connection with the peripheral.

Figure 11:
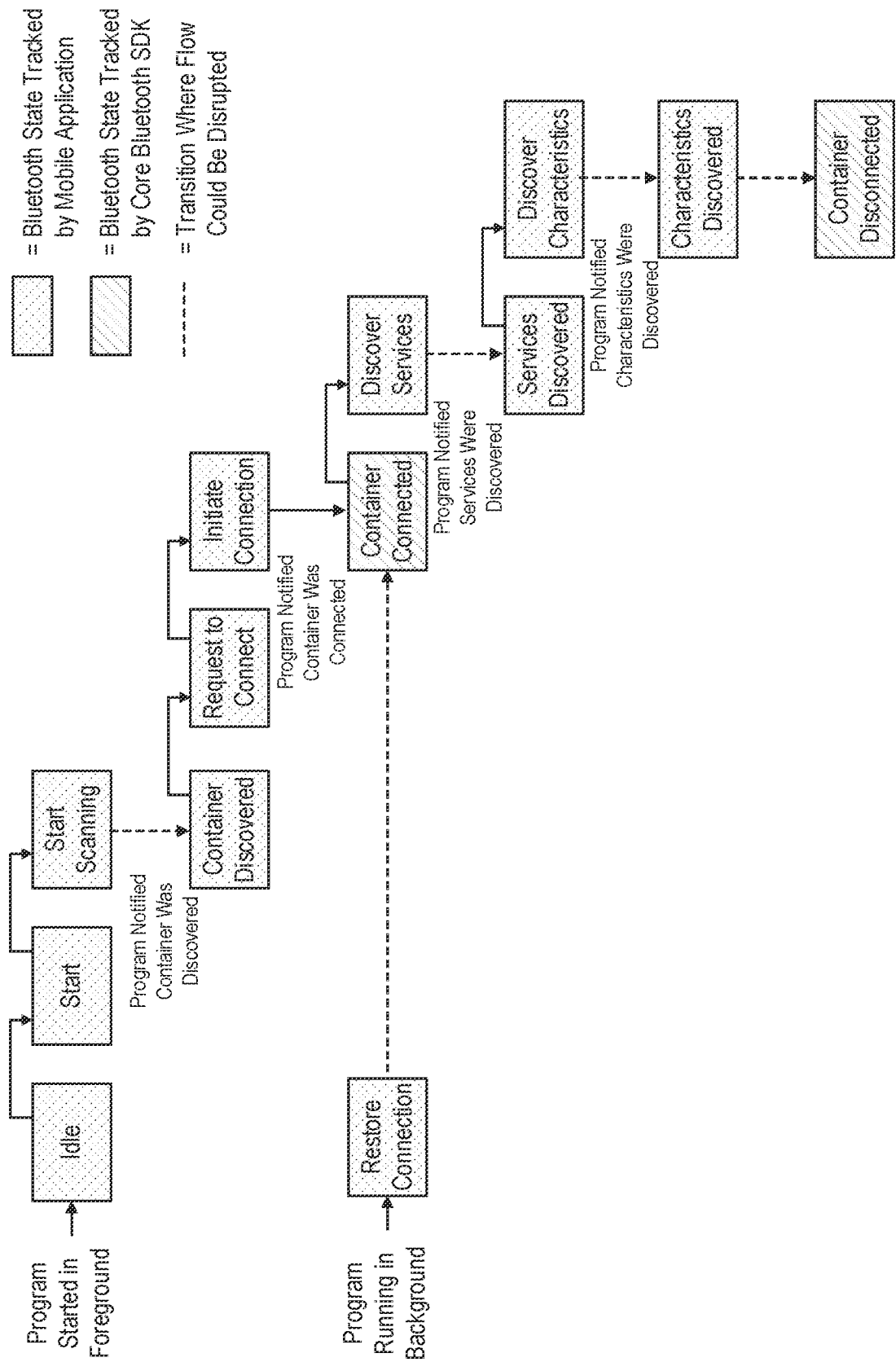
FIG. 11 includes a high-level illustration of a pairing process in which individual steps are tracked by a computer program executing on a computing device.

FIG. 11 includes a high-level illustration of a pairing process in which individual steps are tracked by a computer program executing on a computing device. Much like FIG. 10, the pairing process is described with respect to an iPhone® mobile digital device manufactured by Apple Inc. for the purpose of illustration. As can be seen in FIG. 11, the pairing process is largely similar to the conventional pairing process shown in FIG. 10. Here, however, a mobile application that is executing on the iPhone® mobile digital device is configured to track other states throughout the pairing process. For example, the mobile application may be programmed to track some or all of the states shown in FIG. 11, as well as other states not shown in FIG. 11. Such an approach allows the mobile application to track states in a detailed manner throughout the pairing process.

Figure 12:
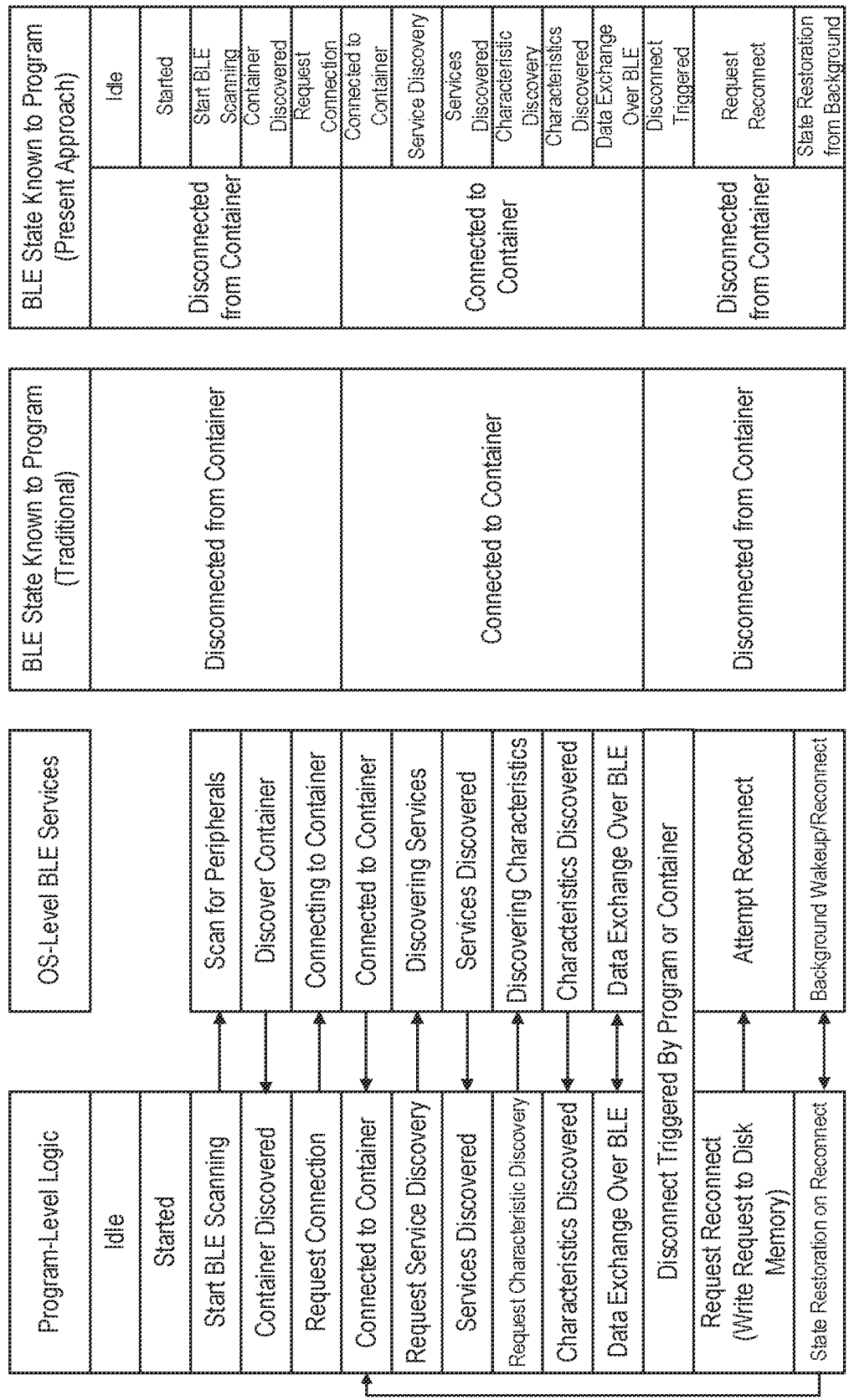
FIG. 12 includes a high-level diagram that illustrates how a computer program, when executed by a computing device, can interface with Bluetooth software development kit (SDK) libraries to track detailed states throughout the pairing process discussed above with reference to FIG. 11

FIG. 12 includes a high-level diagram that illustrates how a computer program, when executed by a computing device, can interface with Bluetooth SDK libraries to track detailed states throughout the pairing process discussed above with reference to FIG. 11. These detailed states provide greater insight into connectivity status than those that would be traditionally surfaced to the computer program through the operating system. This not only allows the computing device to efficiently handle unexpected silent errors and disconnections within the Bluetooth protocol stack, but also at the operating system level.

Figure 13:
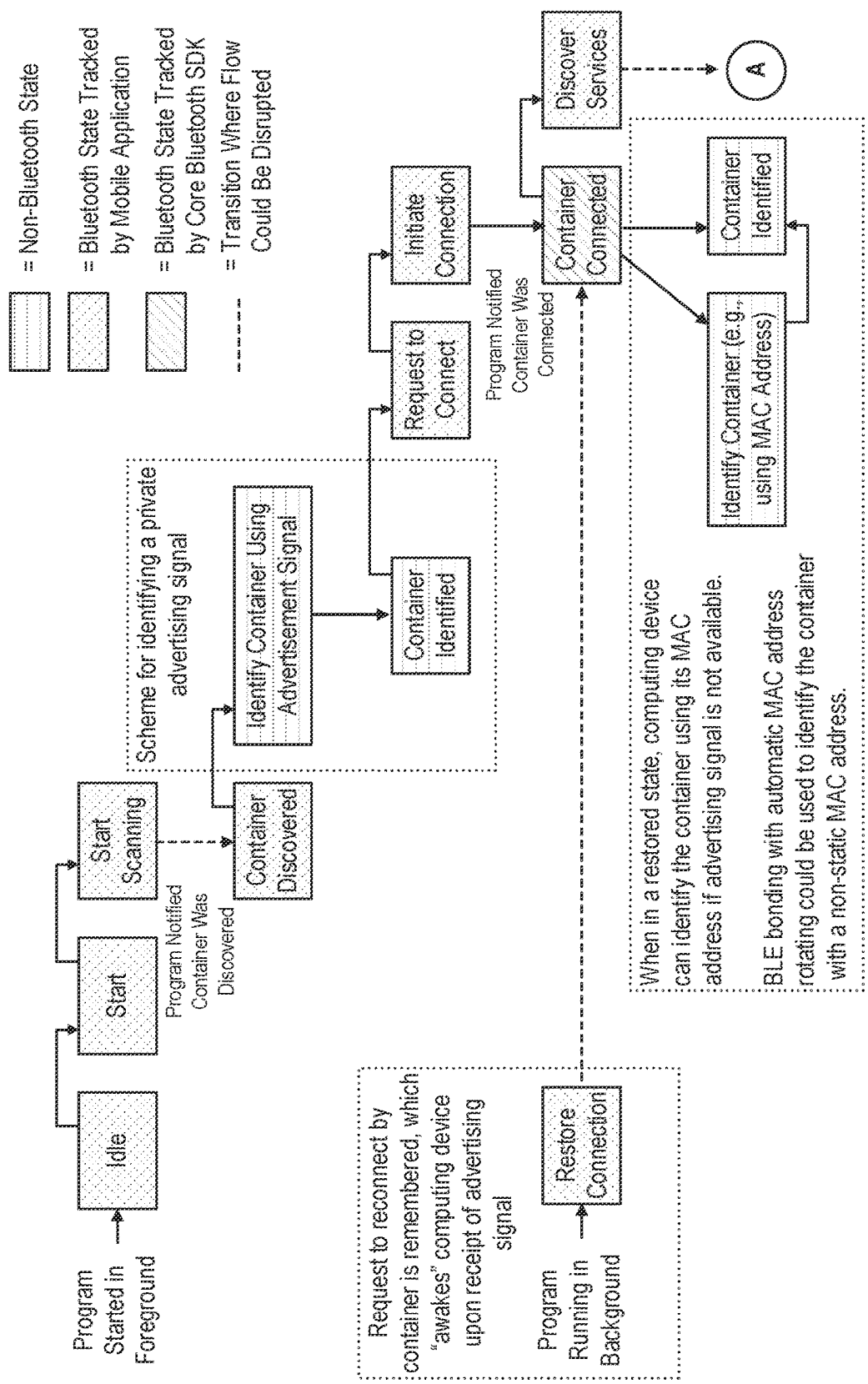
FIG. 13 includes a high-level illustration of another approach to tracking the state that involves private advertising.

FIG. 13 includes a high-level illustration of another approach to tracking the state that involves private advertising. While the approach shown in FIG. 13 is similar to the approach shown in FIG. 11, there are several differences. Upon discovering the container, the computing device may employ a scheme for establishing its identity as shown in FIG. 13. This scheme may permit the computing device to identify the container based on the content of its advertising signal discovered through scanning while disabling tracking by third parties. Moreover, when in a restored state, the computing device may identify the container using its media access control (MAC) address since its advertising signal may not be available. The term "restored state," as used herein, refers to the situation where a computing device connects to a container with which the computing device previously connected. In this situation, the computing device may be said to be "restoring" the wireless communication channel. In some embodiments, the computing device may employ a password-based pairing scheme to secure the wireless communication channel. As shown in FIG. 13, this is normally performed after the characteristics of the container have been established.

To ensure that the container can be reconnected with the computing device without issue, the computing device may be programmed to ensure that the container is remembered. For example, the computing device may ensure that the container is remembered for future synchronization events by requesting disconnects at the messaging layer rather than the Bluetooth connection layer before writing a reconnection request to disk storage. More specifically, the computing device can write a reconnection request to its disk storage. Because the computer program can be shut down by the operating system of the computing device, this request can guarantee that reconnection will occur if the computer program is shut down since the request lives beyond the computer program. Such an approach ensures that the computing device is able to reliably reconnect to the container in the background, even if the container is one whose connectivity is inconsistent due to, for example, power-saving features and the computing device is one whose memory could be cleared at any time.

Figure 14:
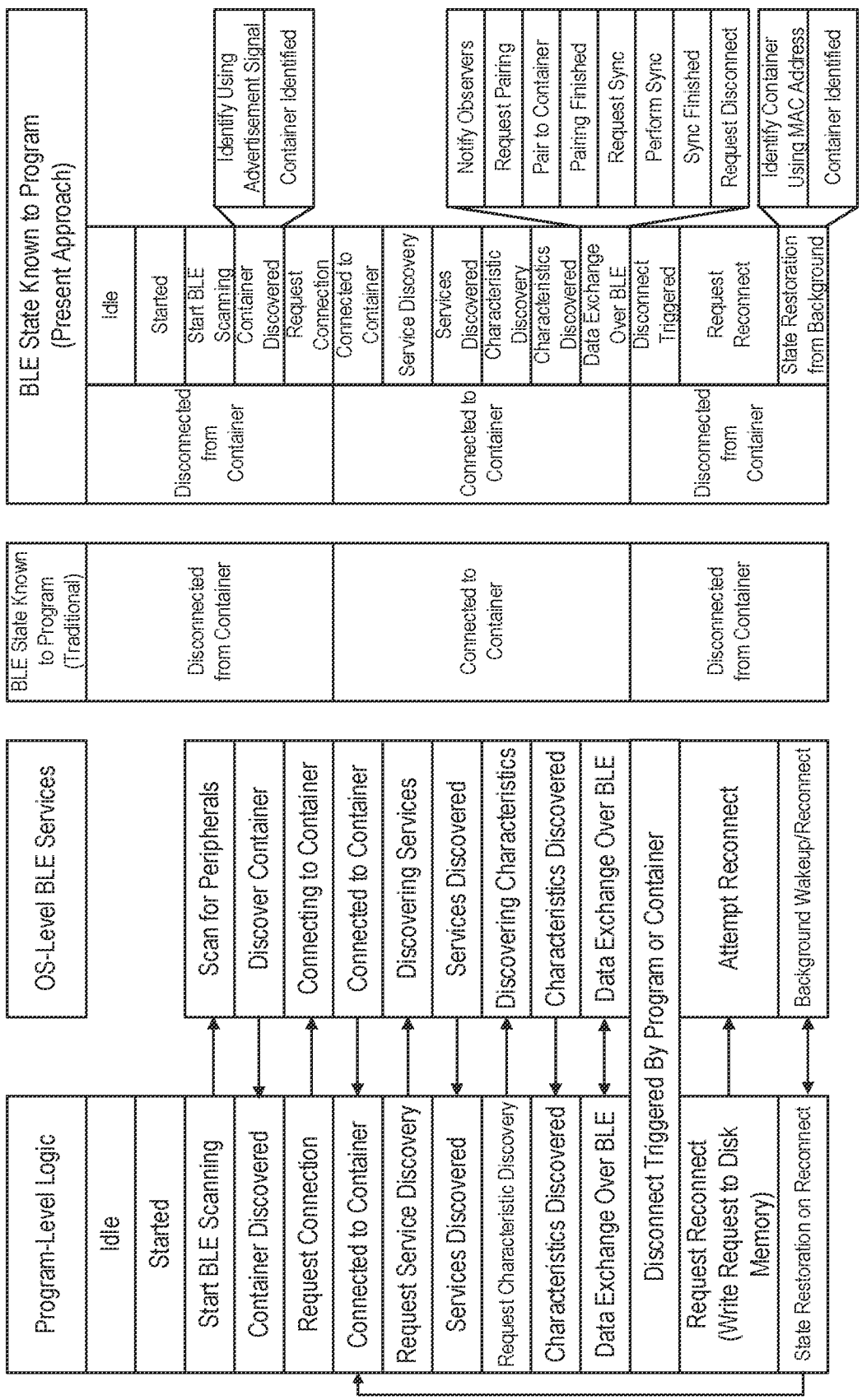
FIG. 14 includes a high-level diagram that illustrates how a computer program, when executed by a computing device, can interface with a Bluetooth SDK to track detailed states throughout the pairing process discussed above with reference to FIG. 13.

FIG. 14 includes a high-level diagram that illustrates how a computer program, when executed by a computing device, can interface with a Bluetooth SDK to track detailed states throughout the pairing process discussed above with reference to FIG. 13. As shown in FIG. 14, the computer program will have insight into all of the states listed in FIG. 12. However, the computing device will also have insight into several additional states related to private advertising and encryption.

Note that while the approaches shown in FIGS. 10-14 are described in the context of facilitating the transfer of data from a container with medication stored therein to a computing device, aspects of the technology could be used to improve the reliability of communications between any pair of computing devices. For example, the wrapper for improving the reliability of connections established in accordance with short-range communication protocols could be implemented in a first computing device (e.g., a wearable electronic device) that is interested in more reliably transferring data to a second computing device (e.g., a mobile phone).

Processing System

Figure 15:
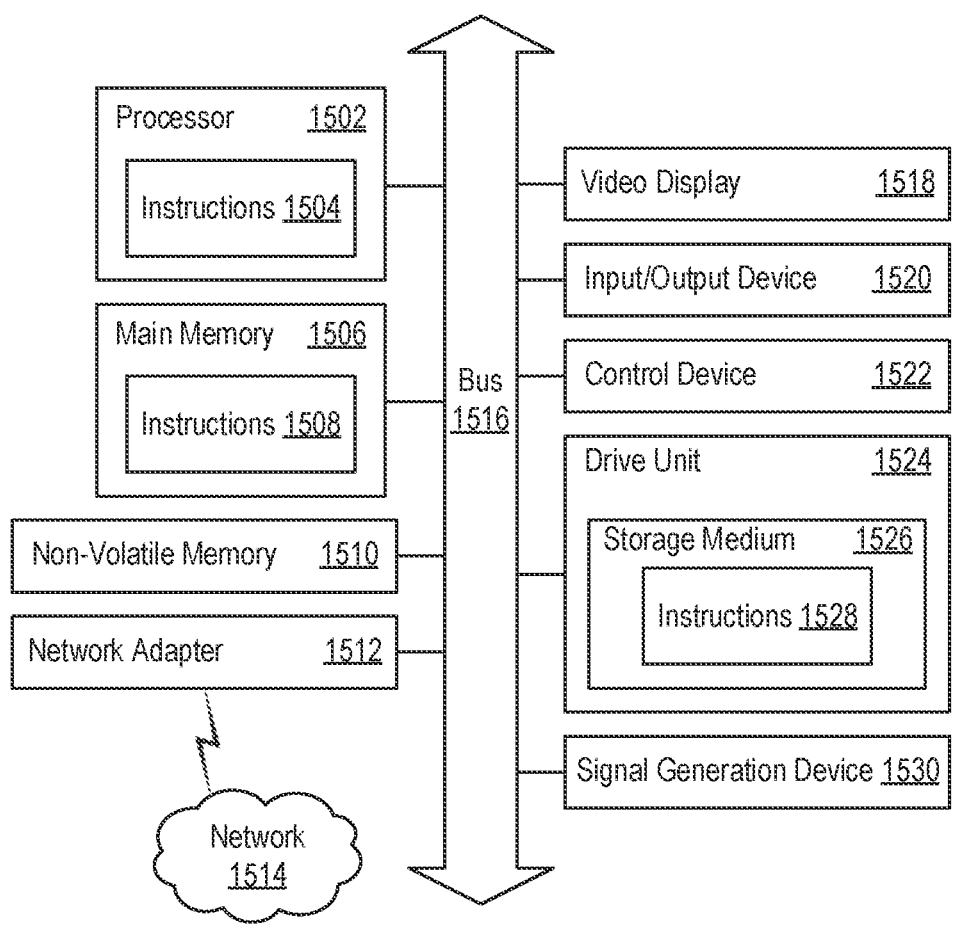
FIG. 15 is a block diagram illustrating an example of a processing system in which at least some operations described herein can be implemented.

FIG. 15 is a block diagram illustrating an example of a processing system 1500 in which at least some operations described herein can be implemented. For example, some components of the processing system 1500 may be hosted on a container (e.g., containers 100A-B of FIGS. 1A-B, container 200 of FIG. 2, or container 300 of FIG. 3). As another example, some components of the processing system 1500 may be hosted on a computing device that is connected to a container across a network.

The processing system 1500 may include one or more central processing units ("processors") 1502, main memory 1506, non-volatile memory 1510, network adapter 1512 (e.g., a network interface), video display 1518, input/output devices 1520, control device 1522 (e.g., a keyboard or pointing device), drive unit 1524 including a storage medium 1526, and signal generation device 1530 that are communicatively connected to a bus 1516. The bus 1516 is illustrated as an abstraction that represents one or more physical buses or point-to-point connections that are connected by appropriate bridges, adapters, or controllers. The bus 1516, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC ($I^2C$) bus, or an Institute of Electrical and Electronics Engineers (IEEE) standard 1394 bus (also referred to as "Firewire").

The processing system 1500 may share a similar processor architecture as that of a desktop computer, tablet computer, mobile phone, game console, music player, wearable electronic device (e.g., a watch or fitness tracker), network-connected ("smart") device (e.g., a television or home assistant device), virtual/augmented reality systems (e.g., a head-mounted display), or another computing device capable of executing a set of instructions (sequential or otherwise) that specify action(s) to be taken by the processing system 1500.

While the main memory 1506, non-volatile memory 1510, and storage medium 1526 are shown to be a single medium, the terms "machine-readable medium" and "storage medium" should be taken to include a single medium or multiple media (e.g., a centralized/distributed database and/or associated caches and servers) that store one or more sets of instructions 1528. The terms "machine-readable medium" and "storage medium" shall also be taken to include any medium that is capable of storing, encoding, or carrying a set of instructions for execution by the processing system 1500.

In general, the routines executed to implement the embodiments of the disclosure may be implemented as part of an operating system or a specific application, component, program, object, module, or sequence of instructions (collectively referred to as "computer programs"). The computer programs typically comprise one or more instructions (e.g., instructions 1504, 1508, 1528) set at various times in various memory and storage devices in a computing device. When read and executed by the processors 1502, the instruction(s) cause the processing system 1500 to perform operations to execute elements involving the various aspects of the present disclosure.

Moreover, while embodiments have been described in the context of fully functioning computing devices, those skilled in the art will appreciate that some aspects of the technology are capable of being distributed as a program product in a variety of forms. The present disclosure applies regardless of the particular type of machine- or computer-readable media used to effect distribution.

Further examples of machine- and computer-readable media include recordable-type media, such as volatile and non-volatile memory devices 1110, removable disks, hard disk drives, and optical disks (e.g., Compact Disk Read-Only Memory (CD-ROMS) and Digital Versatile Disks (DVDs)), and transmission-type media, such as digital and analog communication links.

The network adapter 1512 enables the processing system 1500 to mediate data in a network 1514 with an entity that is external to the processing system 1500 through any communication protocol supported by the processing system 1500 and the external entity. The network adapter 1512 can include a network adaptor card, a wireless network interface card, a router, an access point, a wireless router, a switch, a multilayer switch, a protocol converter, a gateway, a bridge, bridge router, a hub, a digital media receiver, a repeater, or any combination thereof.

The network adapter 1512 may include a firewall that governs and/or manages permission to access/proxy data in a network. The firewall may also track varying levels of trust between different machines and/or applications. The firewall can be any number of modules having any combination of hardware, firmware, or software components able to enforce a predetermined set of access rights between a set of machines and applications, machines and machines, or applications and applications (e.g., to regulate the flow of traffic and resource sharing between these entities). The firewall may additionally manage and/or have access to an access control list that details permissions including the access and operation rights of an object by an individual, a machine, or an application, and the circumstances under which the permission rights stand.

REMARKS

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling those skilled in the relevant art to understand the claimed subject matter, the various embodiments, and the various modifications that are suited to the particular uses contemplated.

Although the Detailed Description describes certain embodiments and the best mode contemplated, the technology can be practiced in many ways no matter how detailed the Detailed Description appears. Embodiments may vary considerably in their implementation details, while still being encompassed by the specification. Particular terminology used when describing certain features or aspects of various embodiments should not be taken to imply that the terminology is being redefined herein to be restricted to any specific characteristics, features, or aspects of the technology with which that terminology is associated. In general, the terms used in the following claims should not be construed to limit the technology to the specific embodiments disclosed in the specification, unless those terms are explicitly defined herein. Accordingly, the actual scope of the technology encompasses not only the disclosed embodiments, but also all equivalent ways of practicing or implementing the embodiments.

The language used in the specification has been principally selected for readability and instructional purposes. It may not have been selected to delineate or circumscribe the subject matter. It is therefore intended that the scope of the technology be limited not by this Detailed Description, but rather by any claims that issue on an application based hereon. Accordingly, the disclosure of various embodiments is intended to be illustrative, but not limiting, of the scope of the technology as set forth in the following claims.

What is claimed is:

1. A non-transitory computer-readable medium with instructions stored thereon that, when executed by a processor of a computing device, cause the computing device to perform operations comprising:
discovering a signal that is locally broadcast by a container that has medication stored therein;
determining that the signal indicates data is available for download from the container;
initiating a wireless communication channel over which the data can be acquired from the container; and
receiving, via the wireless communication channel, a plurality of messages from the container that collectively contain the data in corresponding payloads,
wherein the plurality of messages are transmitted to the computing device by the container in order of increasing payload size and decreasing payload priority.

2. The non-transitory computer-readable medium of claim 1, wherein said determining involves parsing the signal to discover whether a flag is present that indicates data has been generated since a most recent transmission of data to the computing device by the container.

3. The non-transitory computer-readable medium of claim 1, wherein the wireless communication channel is established in accordance with a short-range communication protocol.

4. The non-transitory computer-readable medium of claim 1, wherein the priority of each payload is determined based on priority of the data contained therein.

5. The non-transitory computer-readable medium of claim 1, wherein each message includes a flag that indicates whether the data contained in the corresponding payload is deemed to have high or low priority to the computing device.

6. The non-transitory computer-readable medium of claim 1, wherein data regarding administrations of the medication is higher priority than, and thus transmitted before, data regarding status of the container.

7. The non-transitory computer-readable medium of claim 1,
wherein said initiating involves making multiple calls to functionalities provided by a software framework implemented by an operating system of the computing device, and
wherein the operations further comprise:
recording, in real time, that each of the multiple calls has been made to track a connectivity state with respect to the container.

8. The non-transitory computer-readable medium of claim 1,
wherein in order to initiate the wireless communication channel, the processor makes a series of requests to a Bluetooth software development kit (SDK) implemented by an operating system of the computing device, and
wherein said initiating comprises:
recording, in a data structure, each request that was made to the Bluetooth SDK,
determining that connectivity with the container failed, and
establishing a next request to make to the Bluetooth SDK based on a last request recorded in the data structure.

9. A method implemented by a processor of a container from which medication is dispensable, the method comprising:
receiving, by the processor, input indicative of a request from a computing device to initiate a transfer of data that is stored on the container; and
forwarding, by the processor, the data to a Bluetooth Low Energy (BLE) chipset for transmission to the computing device as a plurality of messages,
wherein the plurality of messages include respective payloads that collectively contain the data, and
wherein the plurality of messages are transmitted in order of increasing payload size and decreasing payload priority.

10. The method of claim 9, further comprising:
determining, by the processor, that a wireless connection established by the BLE chipset with the computing device was lost and then regained following transmittal of the plurality of messages; and
forwarding, by the processor, second data to the BLE chipset for transmission to the computing device as a second plurality of messages,
wherein the second plurality of messages include respective payloads that collectively contain the second data, and
wherein the second plurality of messages are transmitted in order of increasing payload size and decreasing payload priority.

11. The method of claim 10, wherein an initial message of the plurality of messages and an initial message of the second plurality of messages have the same payload size.

12. The method of claim 10, wherein an initial message of the plurality of messages and an initial message of the second plurality of messages have a minimum payload size that is programmed in the container or a computer program executing in the computing device.

13. The method of claim 9, wherein the payload size of the plurality of messages increases linearly up to a threshold value.

14. The method of claim 9, wherein the payload size of the plurality of messages increases exponentially up to a threshold value.

15. The method of claim 9, wherein data related to administrations of the medication is higher priority than, and thus transmitted before, data related to status of the container.

16. The method of claim 9, wherein data related to more recent administrations of the medication is higher priority than, and thus transmitted before, less recent administrations of the medication.

17. The method of claim 9, further comprising:
determining, by the processor, that data of different priority levels is available for transmittal to the computing device;
parsing, by the processor, the data into a series of datasets to be included in the respective payloads of the plurality of messages; and
sorting, by the processor, the series of datasets in order of priority.

* * * * *